United States Patent
Ra

(10) Patent No.: US 11,471,604 B2
(45) Date of Patent: *Oct. 18, 2022

(54) FILTERING SYRINGE

(71) Applicant: Yong-Kuk Ra, Gumi-si (KR)

(72) Inventor: Yong-Kuk Ra, Gumi-si (KR)

( * ) Notice: Subject to any disclaimer, the term of this patent is extended or adjusted under 35 U.S.C. 154(b) by 145 days.

This patent is subject to a terminal disclaimer.

(21) Appl. No.: 15/753,740

(22) PCT Filed: Sep. 6, 2016

(86) PCT No.: PCT/KR2016/009939
§ 371 (c)(1),
(2) Date: Feb. 20, 2018

(87) PCT Pub. No.: WO2017/043830
PCT Pub. Date: Mar. 16, 2017

(65) Prior Publication Data
US 2018/0243510 A1 Aug. 30, 2018

(30) Foreign Application Priority Data

Sep. 9, 2015 (KR) .......... 10-2015-0127942
Mar. 22, 2016 (KR) .......... 10-2016-0034288

(51) Int. Cl.
*A61M 5/31* (2006.01)
*A61M 5/165* (2006.01)
(Continued)

(52) U.S. Cl.
CPC .......... *A61M 5/3145* (2013.01); *A61M 5/165* (2013.01); *A61M 5/31* (2013.01);
(Continued)

(58) Field of Classification Search
CPC ...... A61M 5/3145; A61M 5/165; A61M 5/32; A61M 5/3202; A61M 5/34; A61M 5/349;
(Continued)

(56) References Cited

U.S. PATENT DOCUMENTS 4,180,071 A 12/1979 Oiwa
5,478,328 A * 12/1995 Silverman ............... A61M 5/32
604/110

(Continued)

FOREIGN PATENT DOCUMENTS

CN 103006437 4/2013
KR 10-0981586 9/2010
(Continued)

OTHER PUBLICATIONS

Translation of the description of KR-101335979-B1 (Year: 2013).*
International Search Report for International Application No. PCT/KR2016/009939, dated Nov. 21, 2016.

*Primary Examiner* — Tiffany Legette
*Assistant Examiner* — Antarius S Daniel
(74) *Attorney, Agent, or Firm* — LRK Patent Law Firm

(57) ABSTRACT

The present invention relates to a filtering syringe, and more particularly, to an apparatus obtained by improving a syringe provided with a filter means for filtering foreign substances such as glass fragments of an ampoule, so as to prevent an injection needle or an injection flow passage from being contaminated with the foreign substances while allowing a liquid medicine to be smoothly sucked with a smaller force. The filtering syringe is configured such that the injection needle or the injection flow passage is isolated from the suction flow passage which is upstream of the filter means and in which the foreign substances may remain together with the liquid medicine, thereby allowing the liquid medicine to be sucked with a force less than that required for a conventional syringe and thus maximizing user's convenience and marketability of the syringe.

2 Claims, 21 Drawing Sheets

(51) Int. Cl.
*A61M 5/32* (2006.01)
*A61M 5/34* (2006.01)

(52) U.S. Cl.
CPC ............ *A61M 5/3129* (2013.01); *A61M 5/32* (2013.01); *A61M 5/3202* (2013.01); *A61M 5/3293* (2013.01); *A61M 5/34* (2013.01); *A61M 5/349* (2013.01); *A61M 2005/3114* (2013.01); *A61M 2005/3128* (2013.01); *A61M 2205/7545* (2013.01); *A61M 2206/18* (2013.01)

(58) Field of Classification Search
CPC ........ A61M 5/3293; A61M 2005/3117; A61M 2005/3118; A61M 2005/3201; A61M 2005/3114; A61M 2005/3128; A61M 2205/75; A61M 2205/7545; A61M 2206/18; A61J 1/20; A61J 1/2037; A61J 1/2013; A61J 1/201; A61J 1/2079
See application file for complete search history.

(56) References Cited

U.S. PATENT DOCUMENTS

| | | | |
|---|---|---|---|
| 6,524,278 B1 * | 2/2003 | Campbell | A61J 1/2096 |
| | | | 604/110 |
| 2012/0179096 A1 * | 7/2012 | Aeschlimann | A61M 5/32 |
| | | | 604/87 |

FOREIGN PATENT DOCUMENTS

| | | | | |
|---|---|---|---|---|
| KR | 10-2012-0077486 | 7/2012 | | |
| KR | 10-2012-0087587 | 8/2012 | | |
| KR | 10-1247145 | 4/2013 | | |
| KR | 101335979 B1 * | 12/2013 | .......... | A61M 5/3293 |
| KR | 10-1467945 | 12/2014 | | |

* cited by examiner (a)  (b)

FILTERING SYRINGE

TECHNICAL FIELD

The present invention relates to a filtering syringe, and more particularly, to an apparatus obtained by improving a syringe provided with a filter means for filtering foreign substances such as glass fragments of an ampoule, so as to prevent an injection needle or an injection flow passage from being contaminated with the foreign substances while allowing a liquid medicine to be smoothly sucked with a smaller force, wherein the apparatus is configured such that the injection needle or the injection flow passage is isolated from a suction flow passage which is upstream of the filter means and in which the foreign substances may remain together with the liquid medicine, and such that the filter means and a one-way valve means responsible for a larger force required when the liquid medicine is sucked are externally provided, thereby allowing the liquid medicine to be sucked with a force less than that required for a conventional syringe and thus maximizing user's convenience and marketability of the syringe.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward.

In this conventional syringe, as the plunger 30 is moved backward, a negative pressure is generated in the cylinder 20 and the cylinder is then filled with an injection liquid. As the plunger is moved forward, the injection liquid in the cylinder 20 is discharged through the injection needle 10 by a positive pressure and then injected into a patient's body.

However, when this conventional syringe is used, there is concern that foreign substances incorporated in the injection liquid itself or foreign substances such as glass particles scattered into and mixed with the injection liquid during a process of breaking and opening an ampoule in which the injection liquid is stored may be injected together with the injection liquid into the patient's body.

To solve this problem, a filtering syringe provided with a filter for filtering foreign substances contained in an injection liquid has been developed.

First, as disclosed in Korean Patent Laid-Open Publication No. 2012-87587, a conventional filtering syringe in which a filter for filtering foreign substances is provided in an injection needle or a cylinder performs a function of filtering foreign substances from an injection liquid sucked into the cylinder.

However, since foreign substances had been stuck to an outer surface of the injection needle introduced into an ampoule when the injection liquid is sucked, or foreign substances incorporated in the injection liquid remaining within the injection needle had not been filtered, it was impossible to fundamentally prevent the foreign substances from being injected together with the injection liquid into a patient's body.

In response thereto, U.S. Pat. No. 4,180,071 discloses an example in which a filter for filtering foreign substances is provided in a cap for covering an injection needle.

FIG. 2 is an exploded perspective view illustrating a conventional filter-cap syringe, and FIG. 3 is a sectional view illustrating a main portion of the conventional filter-cap syringe, wherein FIGS. 2 and 3 illustrate the conventional filter-cap syringe disclosed in U.S. Pat. No. 4,180,071.

Since the conventional filter-cap syringe has a cap 40 provided with an internal filter 41 as shown in FIG. 3 so that foreign substances are filtered by the filter 41 when an injection liquid is sucked, and the cap 40 including the filter 41 is detached from an injection needle 10 upon injection of the injection liquid, there is no concern that foreign substances may be injected.

However, the conventional filter-cap syringe has a technical problem in that since the injection liquid may be sucked into a cylinder 20 only via the minute injection needle 10 after passing through the filter 41 provided in the cap 40, a relatively large force is required for sucking the injection liquid and thus it is very inconvenient to use the syringe.

PRIOR ART DOCUMENT

Korean Patent Laid-Open Publication No. 2012-87587.
U.S. Pat. No. 4,180,071.

DISCLOSURE

Technical Problem

The present invention is conceived to solve these problems, and an object of the present invention is to provide a filtering syringe configured such that an injection needle or an injection flow passage is isolated from a suction flow passage which is upstream of a filter means and in which foreign substances may remain together with a liquid medicine, and such that the filter means and a one-way valve means responsible for a larger force required when the liquid medicine is sucked are externally provided, thereby allowing the liquid medicine to be sucked with a force less than that required for a conventional syringe and thus maximizing user's convenience and marketability of the syringe.

Technical Solution

According to the present invention, there is provided a filtering syringe including an injection needle, a cylinder and a plunger, wherein the filtering syringe further includes a suction flow passage formed from a liquid medicine-container to the cylinder; an injection flow passage formed from the cylinder to the injection needle; a filter means and a one-way valve means provided in the suction flow passage; and a detachable opening/closing means provided in the injection flow passage, wherein a flow passage portion of the suction flow passage extending from the liquid medicine-container to the filter means is formed independently of an outer peripheral surface of the injection needle and the injection flow passage.

Here, an inlet of the suction flow passage and an outlet of the injection flow passage may be coaxially arranged with each other, and an outlet of the suction flow passage and an inlet of the injection flow passage may be shared.

Alternatively, the inlet of the suction flow passage and the outlet of the injection flow passage may not be coaxially arranged with each other, and the outlet of the suction flow passage and the inlet of the injection flow passage may be shared.

Otherwise, the inlet of the suction flow passage and the outlet of the injection flow passage may be coaxially arranged with each other, and the outlet of the suction flow passage and the inlet of the injection flow passage may not be shared.

Alternatively, the inlet of the suction flow passage and the outlet of the injection flow passage may not be coaxially arranged with each other, and the outlet of the suction flow passage and the inlet of the injection flow passage may not be shared.

Also, the suction flow passage and the injection flow passage may share a 3-way connector.

The outlet of the suction flow passage and the inlet of the injection flow passage are preferably fixed to be directed in different directions or are angle-adjustable.

In addition, it is preferred that an adhesive material for securing a needle body and a hub of the injection needle to each other is accommodated in the opening/closing means, which surrounds the injection needle to maintain airtightness, so that the adhesive material is isolated from the liquid medicine.

Particularly, in the filtering syringe including the injection needle comprised of the needle body and the hub, and the cylinder to which the injection needle is coupled, preferably, the hub of the injection needle is formed with an annular space having an inner wall surface, an outer wall surface and a bottom surface, and the bottom surface is formed with through-holes communicating with the cylinder; a one-way valve means made of an elastic material and having a cylindrical portion and a wing portion is provided on the inner wall surface, and an end of the wing portion is in elastic contact with the outer wall surface; the filter means is provided within the annular space between the one-way valve means and the though-holes; and the filtering syringe further includes a cap comprised of a hollow body with a sharp tip and hermetically coupled to an outer peripheral surface of the hub, wherein the opening/closing means surrounding the needle body is provided within the cap.

It is preferred that the one-way valve means is formed with a projection cooperating with an inner peripheral surface of the cap to promote deformation of the wing portion.

On the contrary, an inner peripheral surface of the cap may be formed with a protrusion cooperating with the one-way valve means to promote deformation of the wing portion.

Advantageous Effects

The filtering syringe of the present invention is configured such that an injection needle or an injection flow passage is isolated from a suction flow passage which is upstream of a filter means and in which foreign substances may remain together with a liquid medicine, and such that the filter means and a one-way valve means responsible for a larger force required when the liquid medicine is sucked are externally provided. Accordingly, the filtering syringe allows the liquid medicine to be sucked with a force less than that required for a conventional syringe and thus maximizes user's convenience and marketability of the syringe.

BEST MODE

Figure 1:
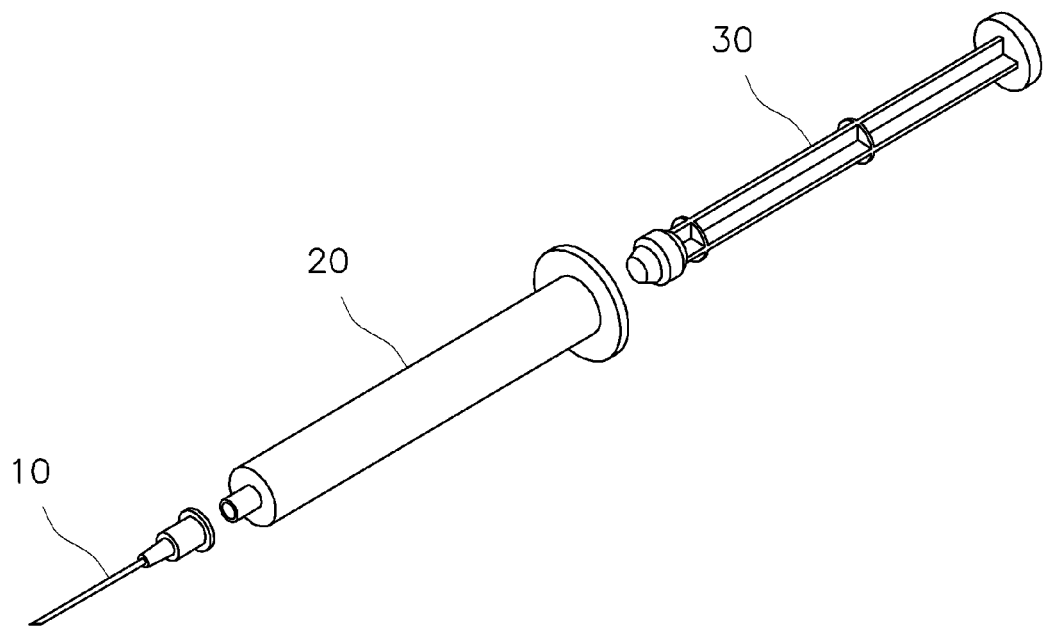
FIG. 1 is an exploded perspective view illustrating a conventional syringe.
Figure 2:
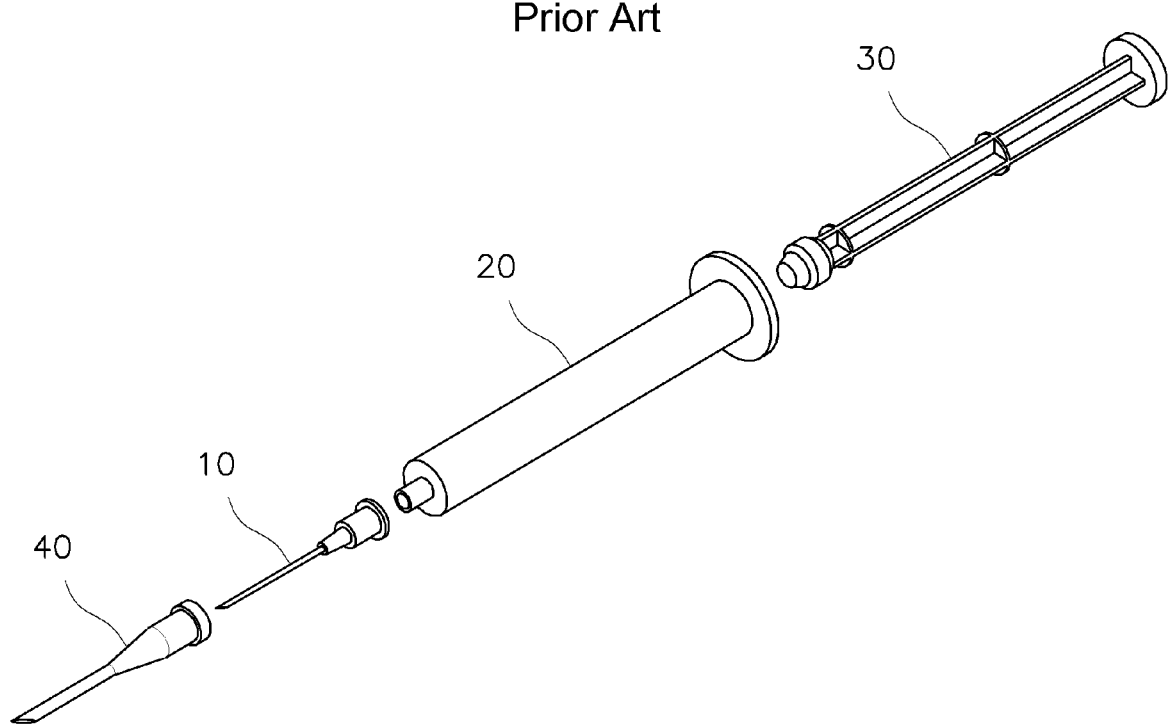
FIG. 2 is an exploded perspective view illustrating a conventional filter-cap syringe.
Figure 3:
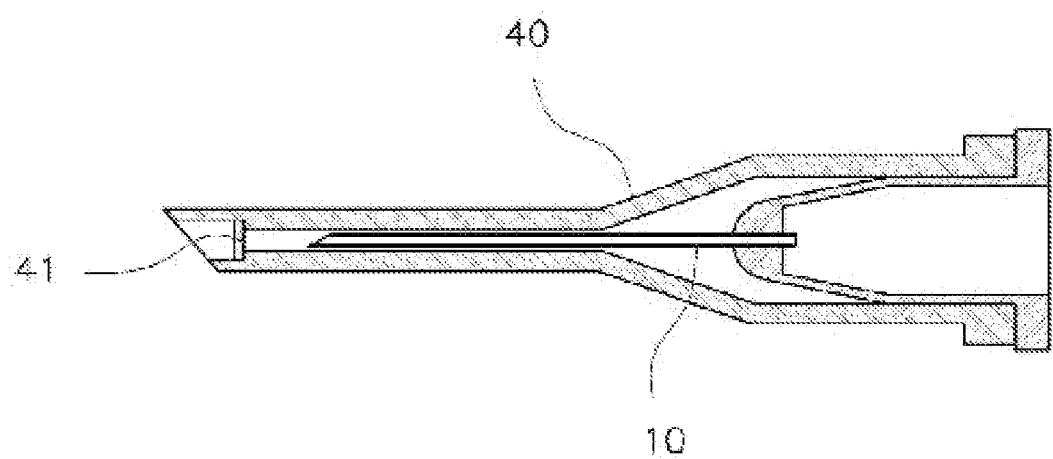
FIG. 3 is a sectional view illustrating a main portion of the conventional filter-cap syringe.
Figure 4:
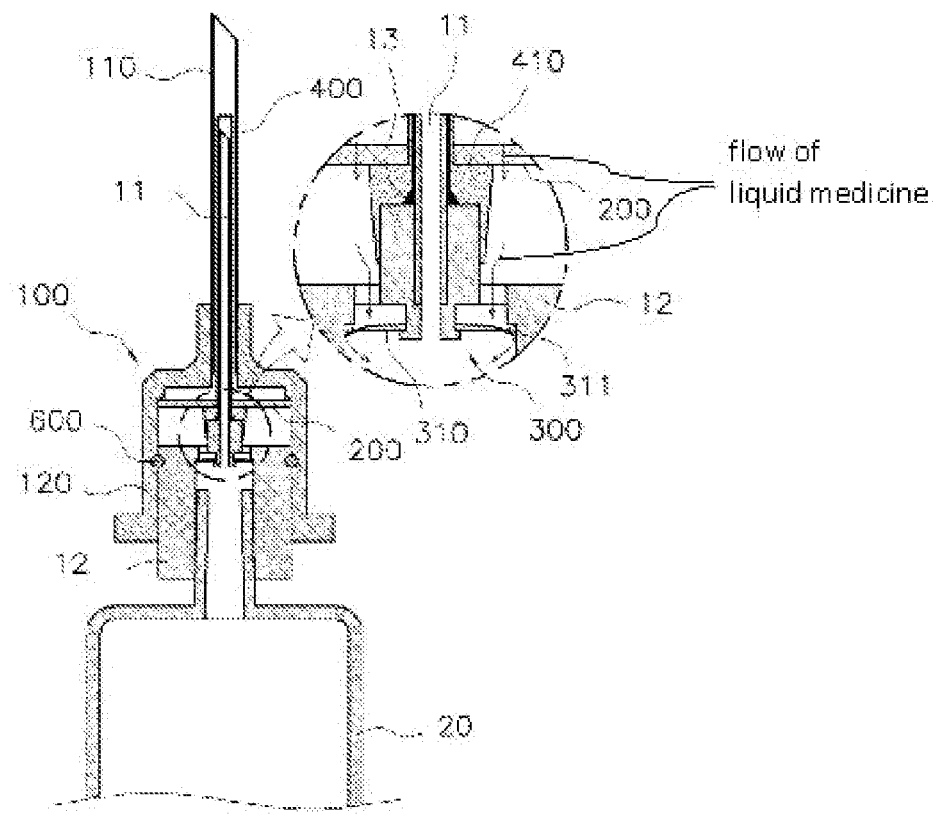
FIG. 4 is a sectional view illustrating a state where a one-way valve means is opened in a first embodiment of a filtering syringe according to the present invention.
Figure 5:
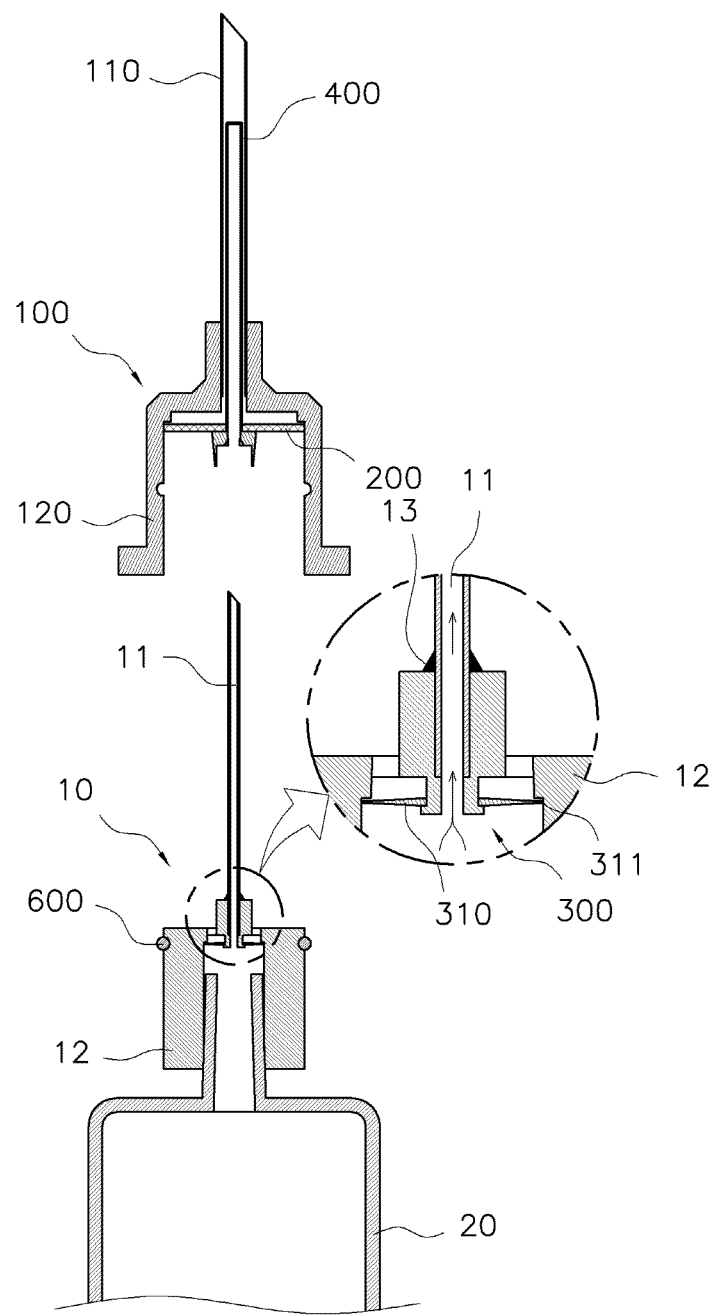
FIG. 5 is a sectional view illustrating a state where the one-way valve means is closed in the first embodiment of the filtering syringe according to the present invention.
Figure 6:
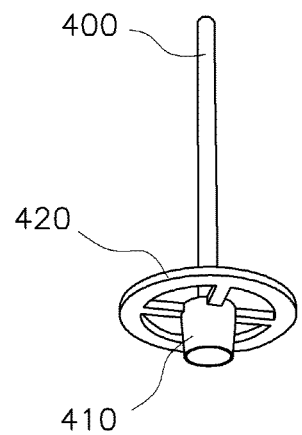
FIG. 6 is a perspective view exemplarily illustrating an opening/closing means in the first embodiment of the filtering syringe according to the present invention.
Figure 10:
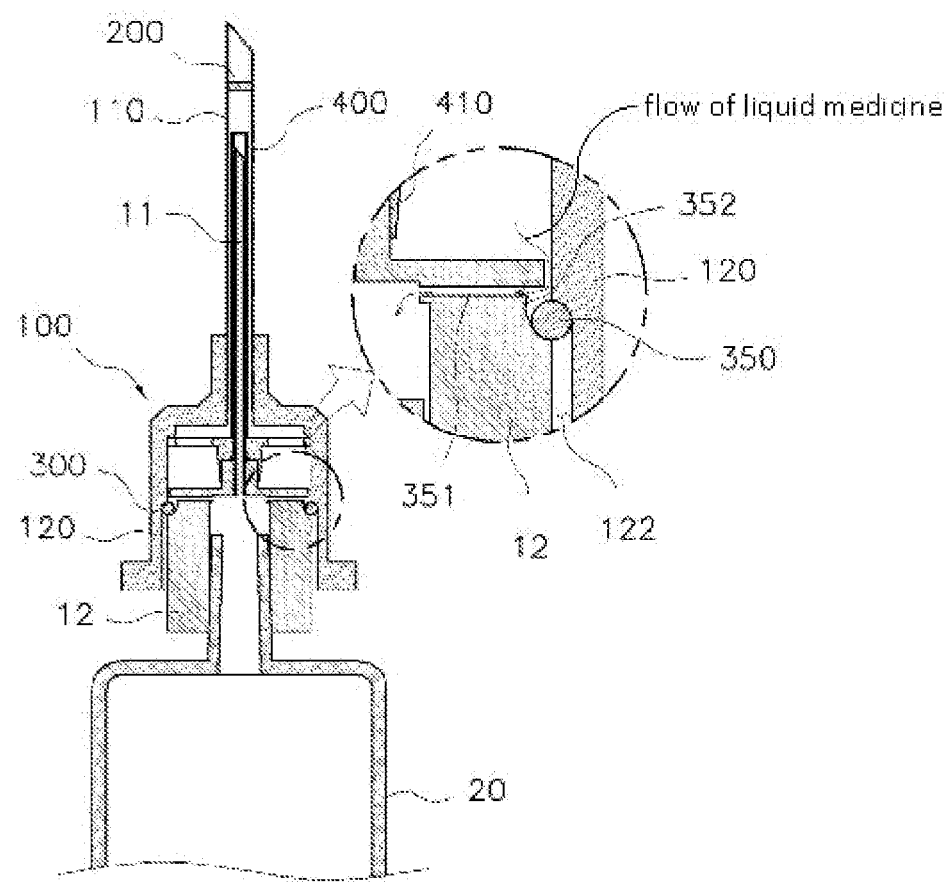
FIG. 10 is a sectional view illustrating a state where the other example of the one-way valve means is opened in the first embodiment of the filtering syringe according to the present invention.
Figure 11:
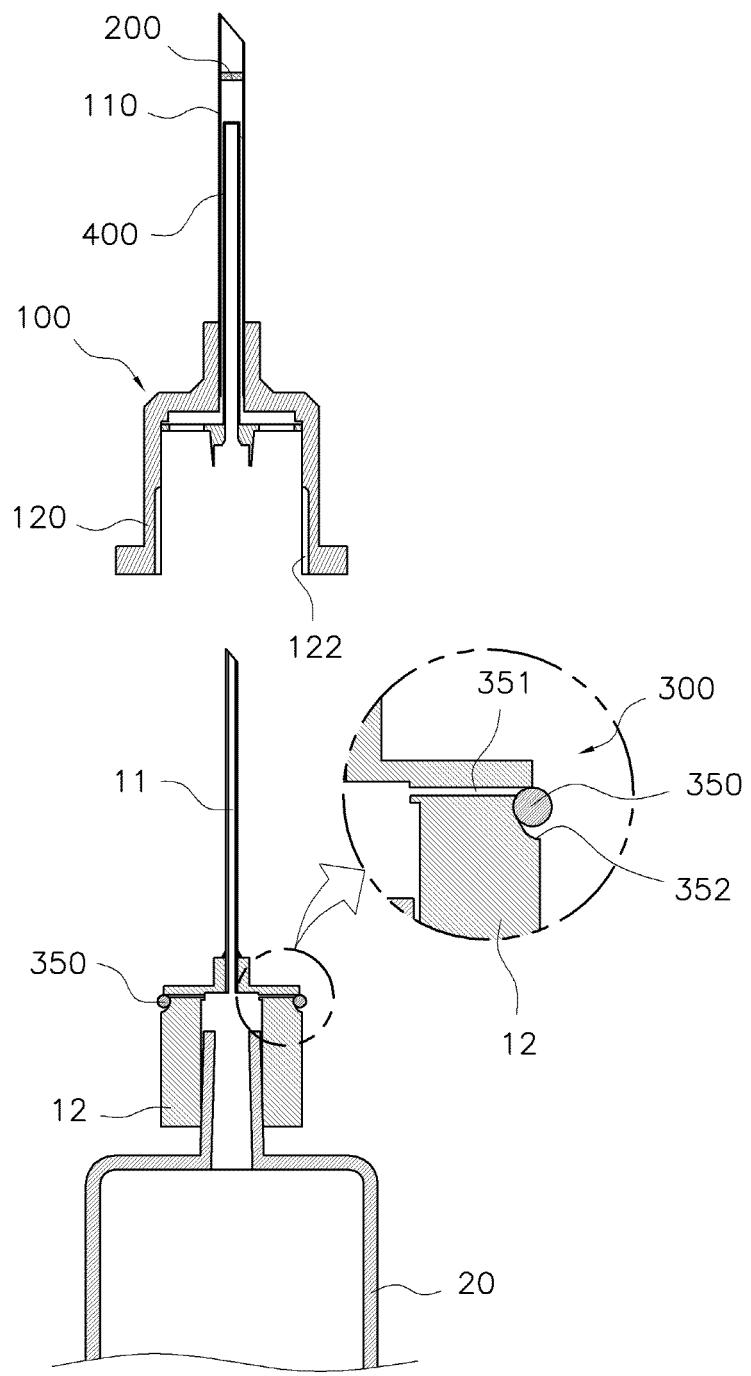
FIG. 11 is a sectional view illustrating a state where the other example of the one-way valve means is closed in the first embodiment of the filtering syringe according to the present invention.
Figure 12:
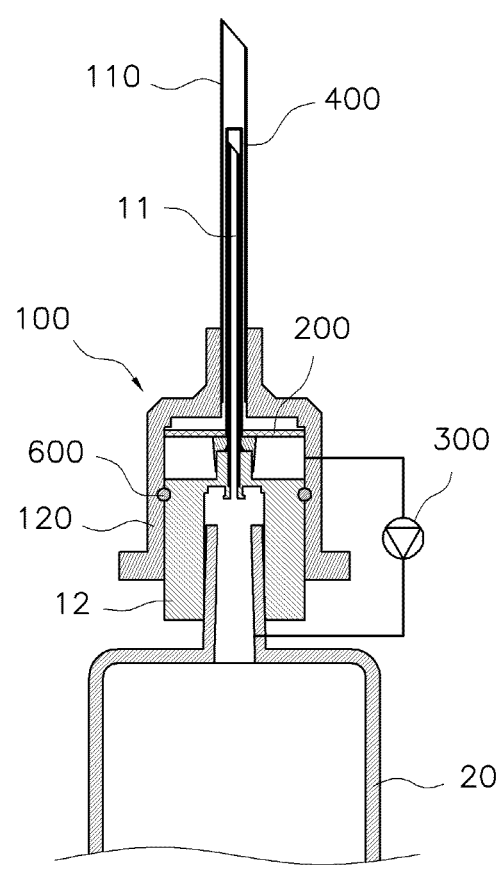
FIG. 12 is a sectional view illustrating a state where the one-way valve means is externally provided in the first embodiment of the filtering syringe according to the present invention.
Figure 13:
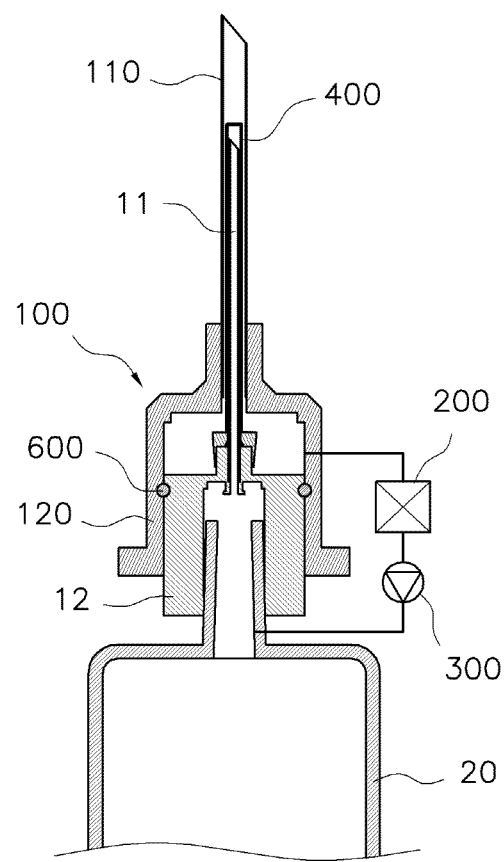
FIG. 13 is a sectional view illustrating a state where a filter means and the one-way valve means are externally provided in the first embodiment of the filtering syringe according to the present invention.
Figure 14:
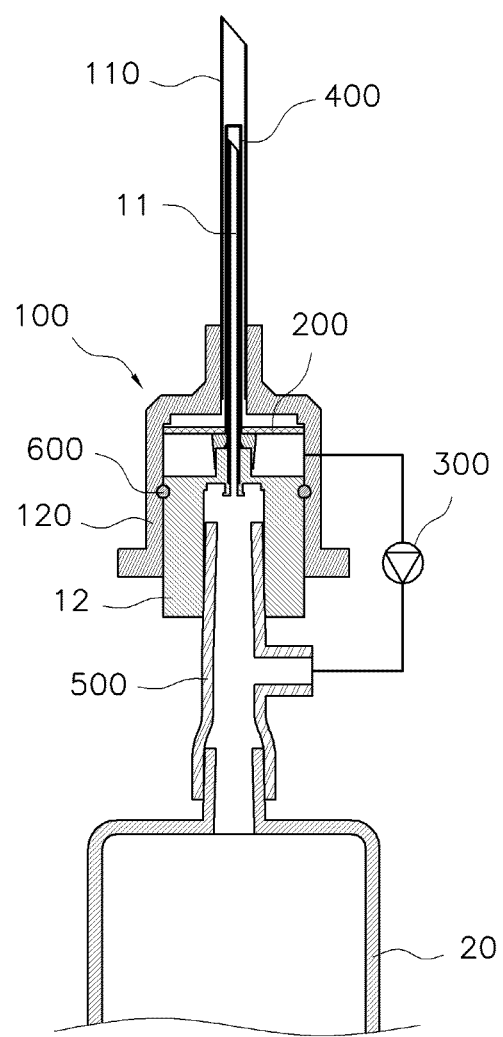
FIG. 14 is a sectional view illustrating a state where the one-way valve means is externally provided and a connector is employed in the first embodiment of the filtering syringe according to the present invention outside.

FIGS. 4 to 14 relate to a first embodiment of a filtering syringe according to the present invention, wherein FIGS. 4 to 11 show a configuration in which a filter means and a one-way valve means are embedded in the filtering syringe and FIGS. 12 to 14 show a configuration in which any one of the filter means and the one-way valve means is externally provided. FIG. 4 is a sectional view illustrating a state where the one-way valve means is opened in the first embodiment of the filtering syringe according to the present invention, FIG. 5 is a sectional view illustrating a state where the one-way valve means is closed in the first embodiment of the filtering syringe according to the present invention, and FIG. 6 is a perspective view exemplarily illustrating an opening/closing means in the first embodiment of the filtering syringe according to the present invention.

Figure 7:
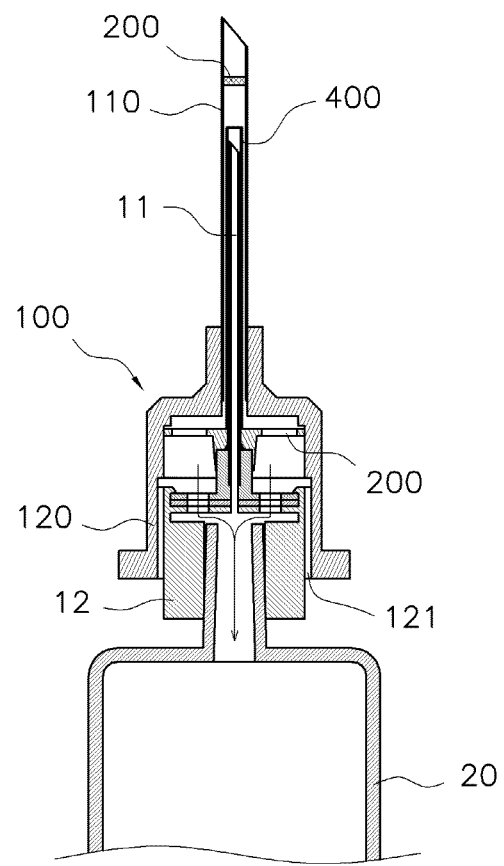
FIG. 7 is a sectional view illustrating a state where another example of the one-way valve means is opened in the first embodiment of the filtering syringe according to the present invention.
Figure 8:
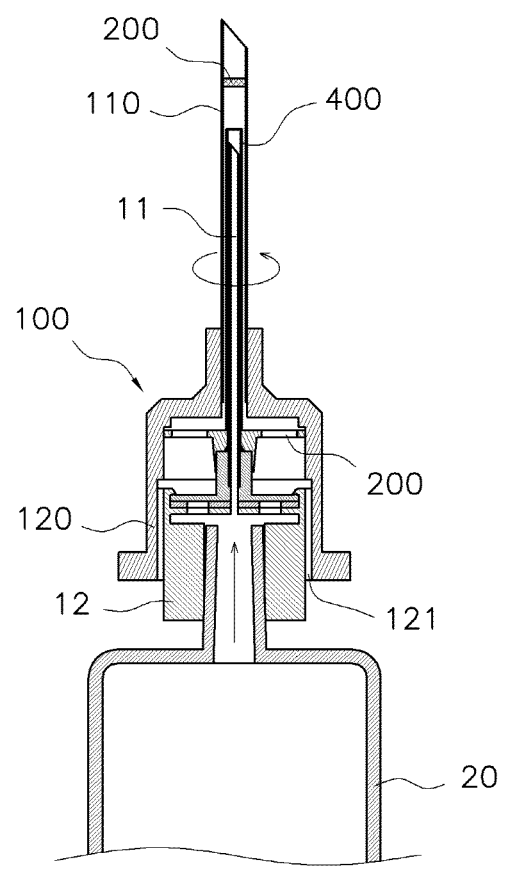
FIG. 8 is a sectional view illustrating a state where another example of the one-way valve means is closed in the first embodiment of the filtering syringe according to the present invention.
Figure 9:
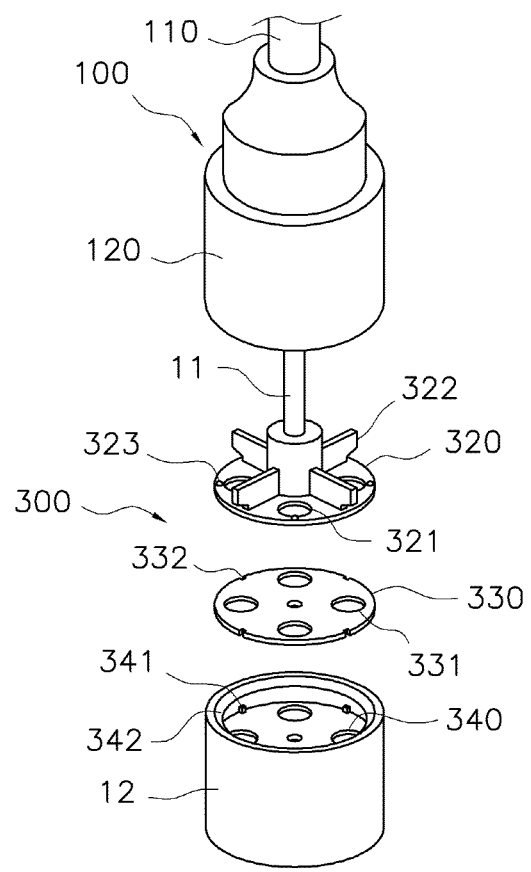
FIG. 9 is an exploded perspective view of a main portion of another example of the one-way valve means in the first embodiment of the filtering syringe according to the present invention.

Moreover, FIG. 7 is a sectional view illustrating a state where another example of the one-way valve means is opened in the first embodiment of the filtering syringe according to the present invention, FIG. 8 is a sectional view illustrating a state where another example of the one-way valve means is closed in the first embodiment of the filtering syringe according to the present invention, and FIG. 9 is an exploded perspective view of a main portion of another example of the one-way valve means in the first embodiment of the filtering syringe according to the present invention.

In addition, FIG. 10 is a sectional view illustrating a state where the other example of the one-way valve means is opened in the first embodiment of the filtering syringe according to the present invention, and FIG. 11 is a sectional view illustrating a state where the other example of the one-way valve means is closed in the first embodiment of the filtering syringe according to the present invention.

Next, FIG. 12 is a sectional view illustrating a state where the one-way valve means is externally provided in the first embodiment of the filtering syringe according to the present invention, FIG. 13 is a sectional view illustrating a state where a filter means and the one-way valve means are externally provided in the first embodiment of the filtering syringe according to the present invention, and FIG. 14 is a sectional view illustrating a state where the one-way valve means is externally provided and a connector is employed in the first embodiment of the filtering syringe according to the present invention outside.

Figure 15:
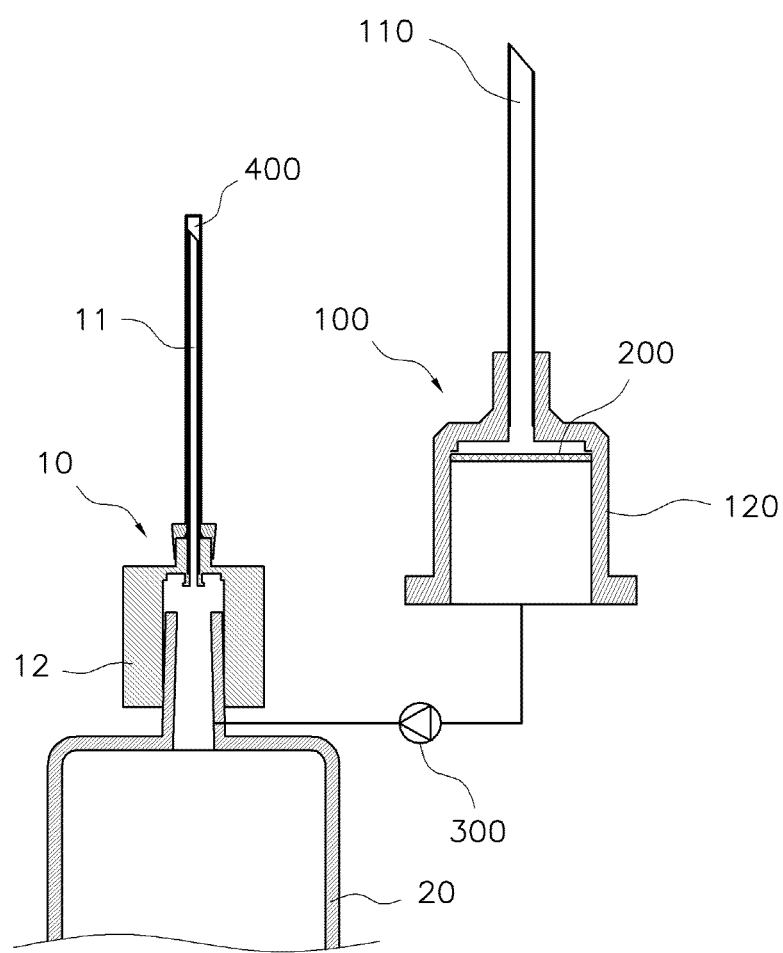
FIG. 15 is a sectional view illustrating a state where a one-way valve means is externally provided in a second embodiment of the filtering syringe according to the present invention.
Figure 16:
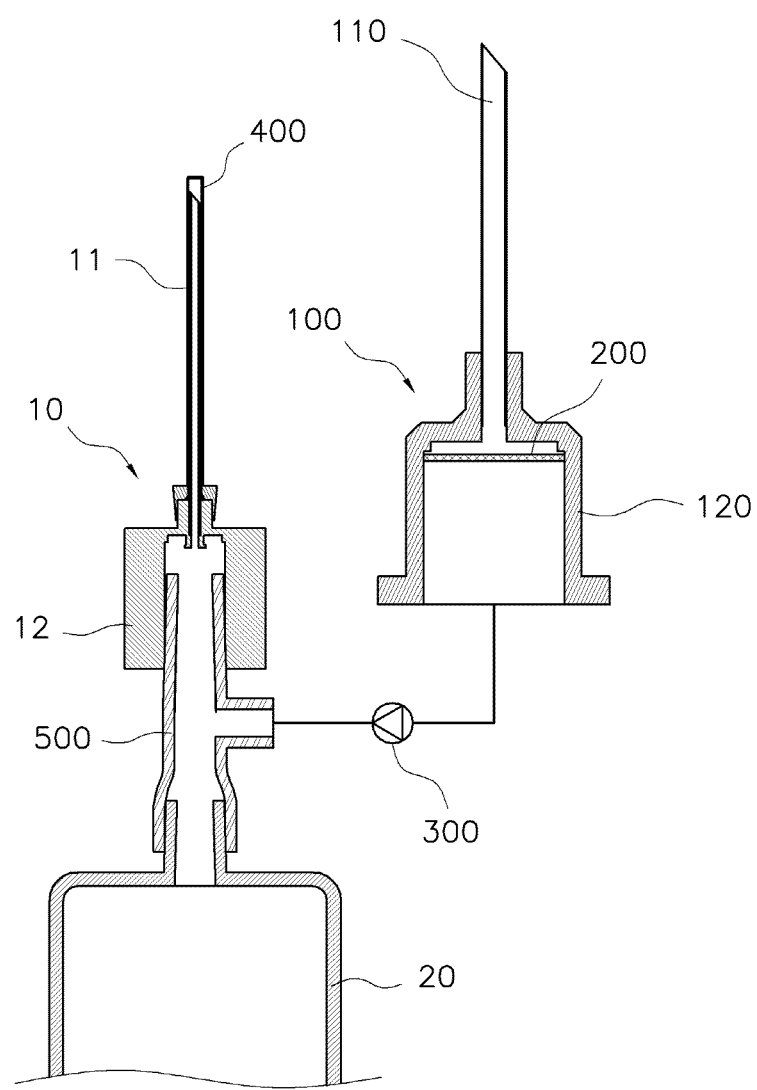
FIG. 16 is a sectional view illustrating a state where the one-way valve means is externally provided and a connector is employed in the second embodiment of the filtering syringe according to the present invention.

Additionally, FIG. 15 is a sectional view illustrating a state where a one-way valve means is externally provided in a second embodiment of the filtering syringe according to the present invention, and FIG. 16 is a sectional view illustrating a state where the one-way valve means is externally provided and a connector is employed in the second embodiment of the filtering syringe according to the present invention.

Figure 17:
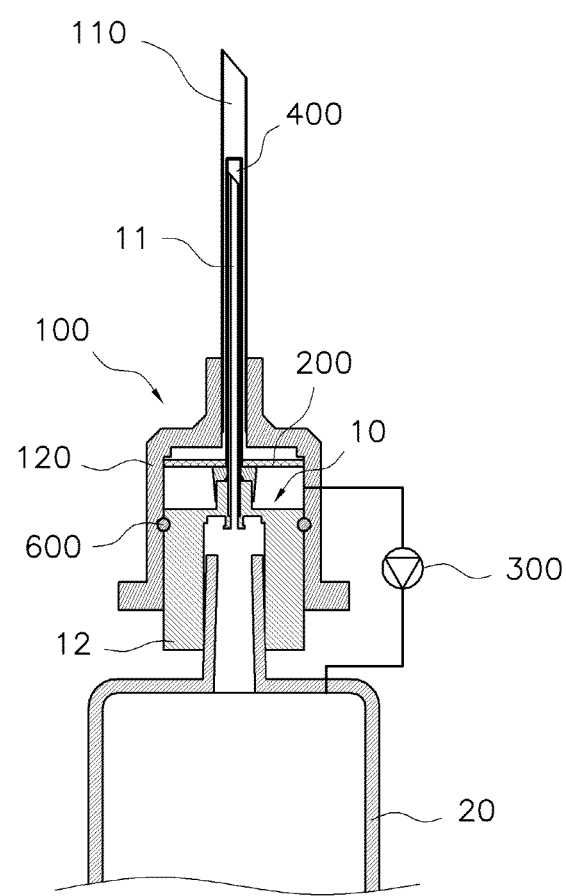
FIG. 17 is a sectional view illustrating a state where a one-way valve means is externally provided in a third embodiment of the filtering syringe according to the present invention.
Figure 18:
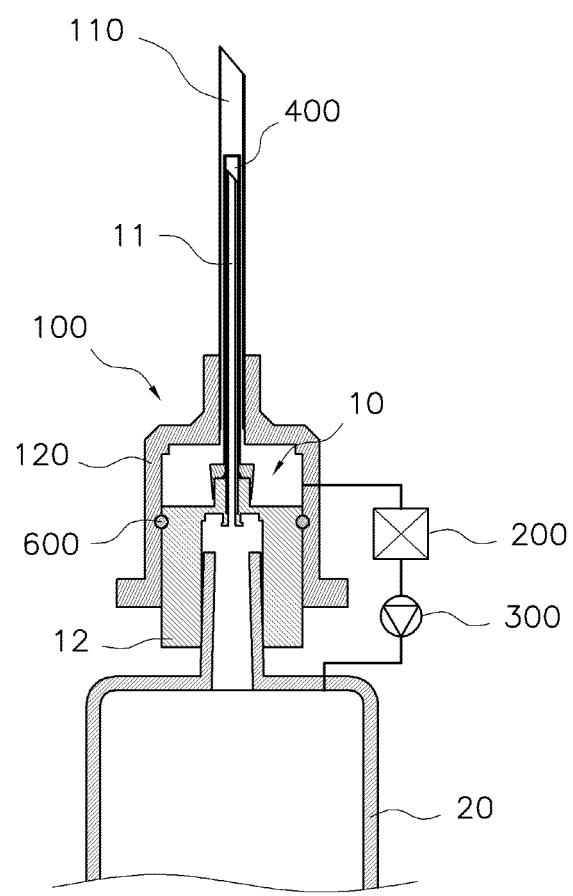
FIG. 18 is a sectional view illustrating a state where a filter means and the one-way valve means are externally provided in the third embodiment of the filtering syringe according to the present invention.

Furthermore, FIG. 17 is a sectional view illustrating a state where a one-way valve means is externally provided in a third embodiment of the filtering syringe according to the present invention, and FIG. 18 is a sectional view illustrating a state where a filter means and the one-way valve means are externally provided in the third embodiment of the filtering syringe according to the present invention.

Figure 19:
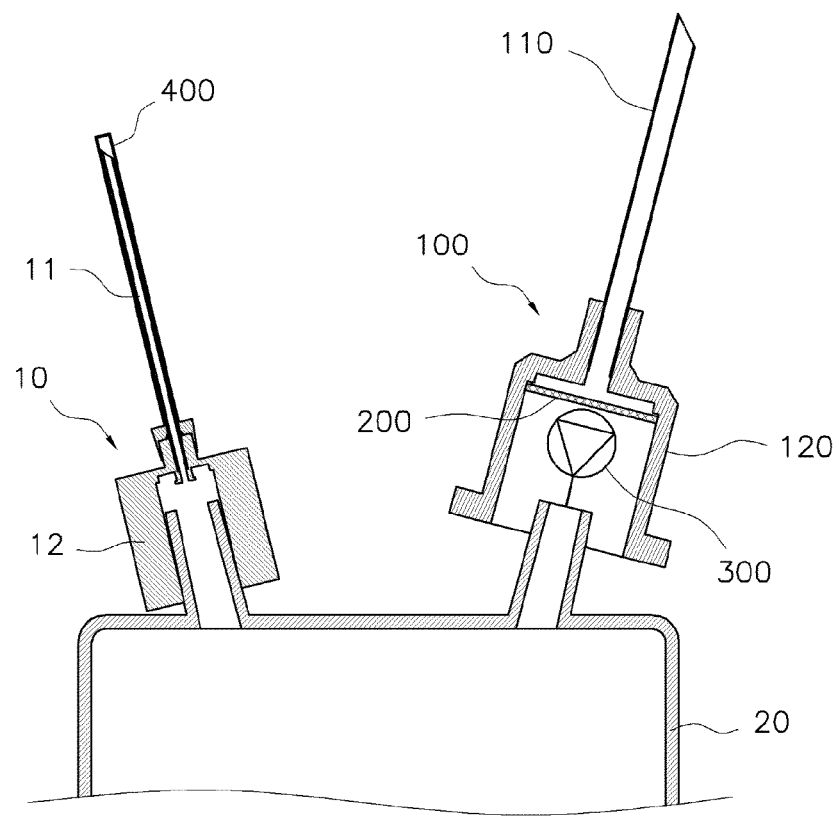
FIG. 19 is a sectional view illustrating a state where a filter means and a one-way valve means are internally provided in a fourth embodiment of the filtering syringe according to the present invention.
Figure 20:
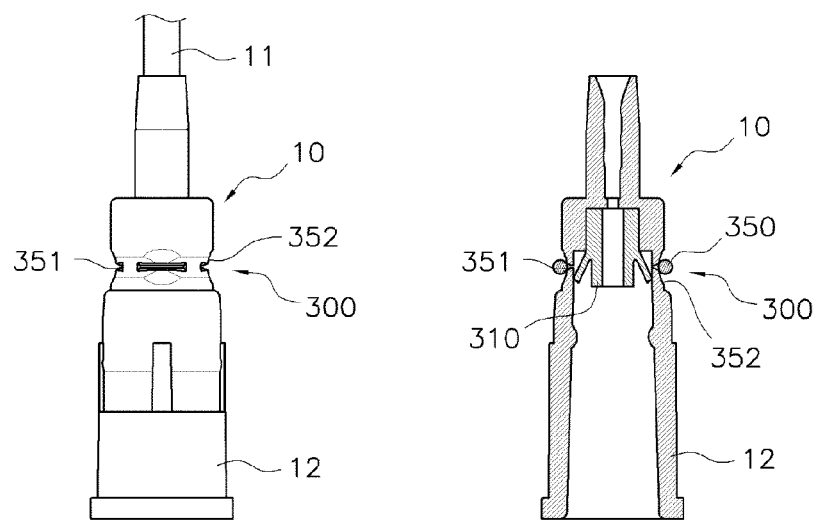
FIGS. 20 (a) and (b) are views illustrating a further example of the one-way valve means in the first embodiment of the filtering syringe according to the present invention.

FIG. 19 is a sectional view illustrating a state where a filter means and a one-way valve means are internally provided in a fourth embodiment of the filtering syringe according to the present invention, and FIG. 20 is views illustrating a further example of the one-way valve means in the first embodiment of the filtering syringe according to the present invention, wherein FIG. 20 (a) is a front view and FIG. 20 (b) is a front sectional view.

Figure 21:
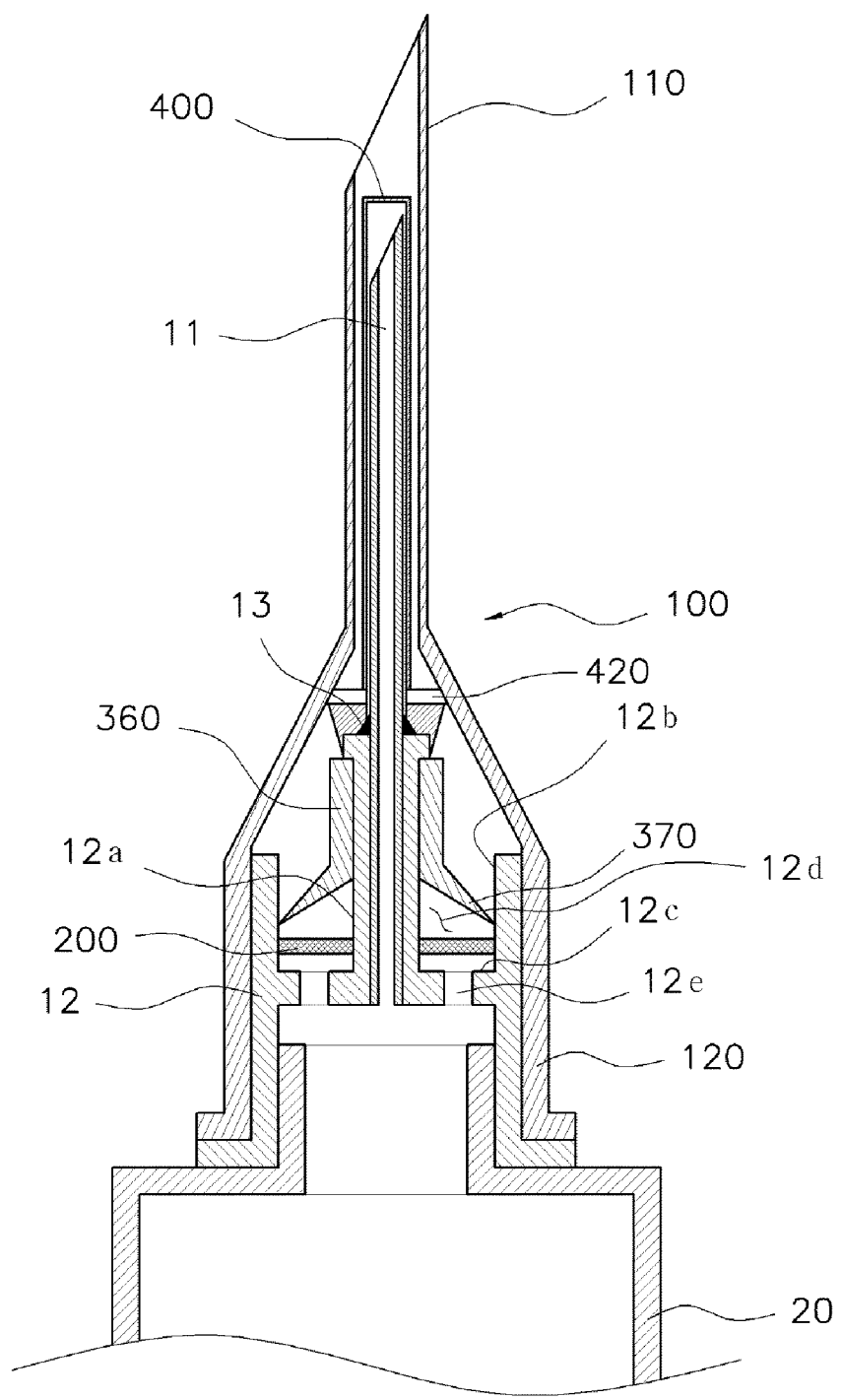
FIG. 21 is a sectional view illustrating another example of the first embodiment of the filtering syringe according to the present invention.
Figure 22:
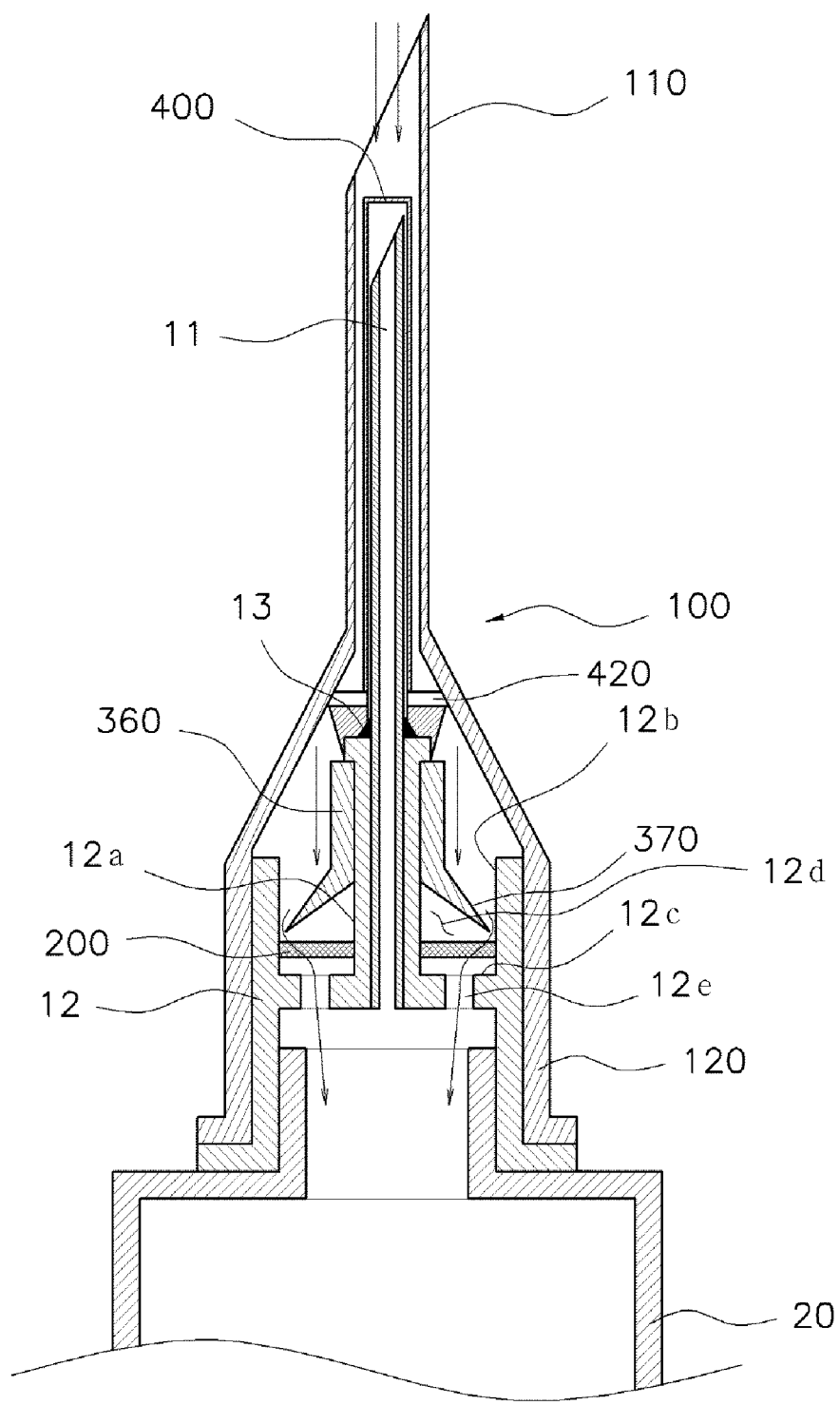
FIG. 22 is a sectional view illustrating a state where a liquid medicine is sucked in another example of the first embodiment of the filtering syringe according to the present invention.
Figure 23:
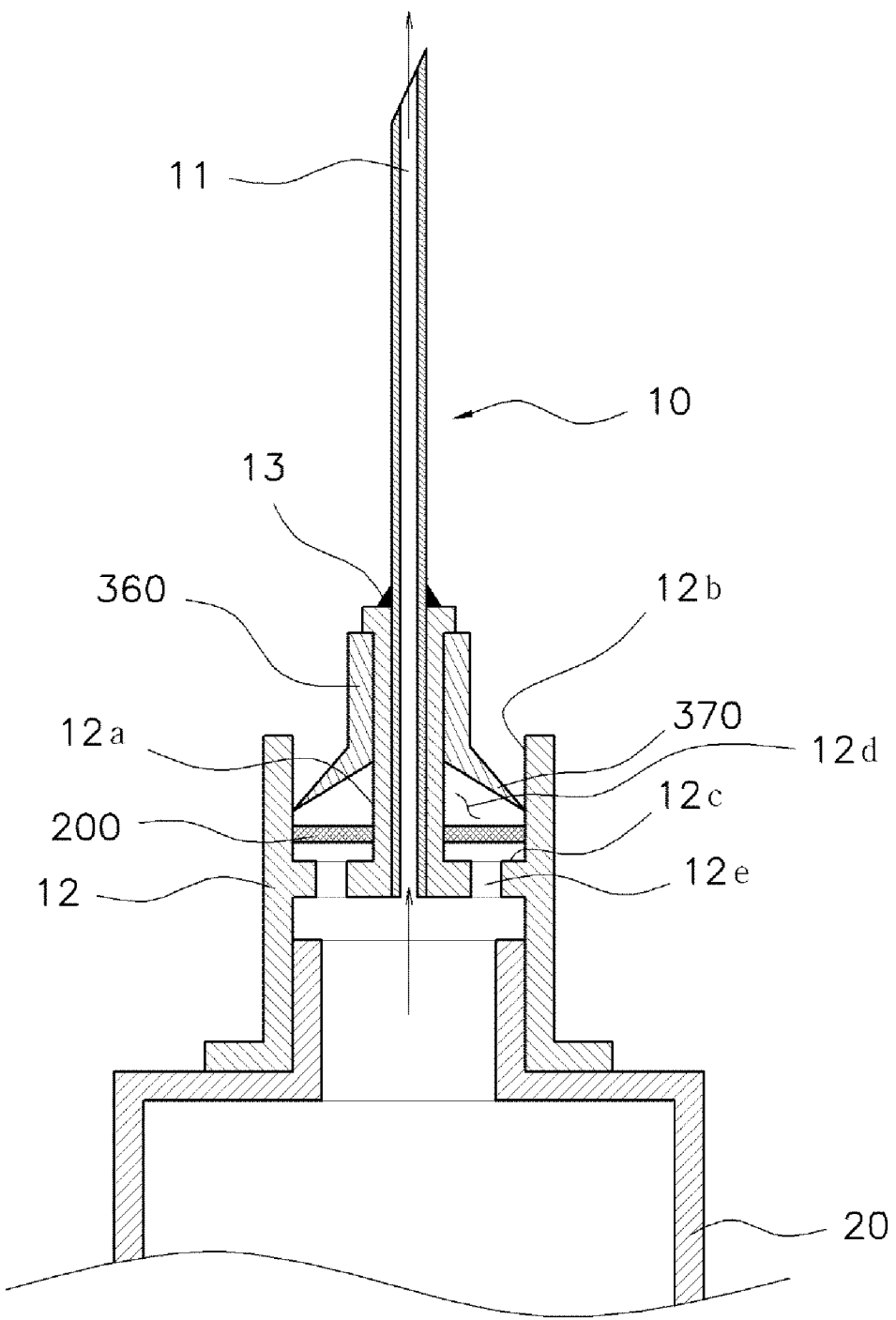
FIG. 23 is a sectional view illustrating a state where the liquid medicine is injected in another example of the first embodiment of the filtering syringe according to the present invention.

Moreover, FIG. 21 is a sectional view illustrating another example of the first embodiment of the filtering syringe according to the present invention, FIG. 22 is a sectional view illustrating a state where a liquid medicine is sucked in another example of the first embodiment of the filtering syringe according to the present invention, and FIG. 23 is a sectional view illustrating a state where the liquid medicine is injected in the another of the first embodiment of the filtering syringe according to the present invention.

Figure 24:
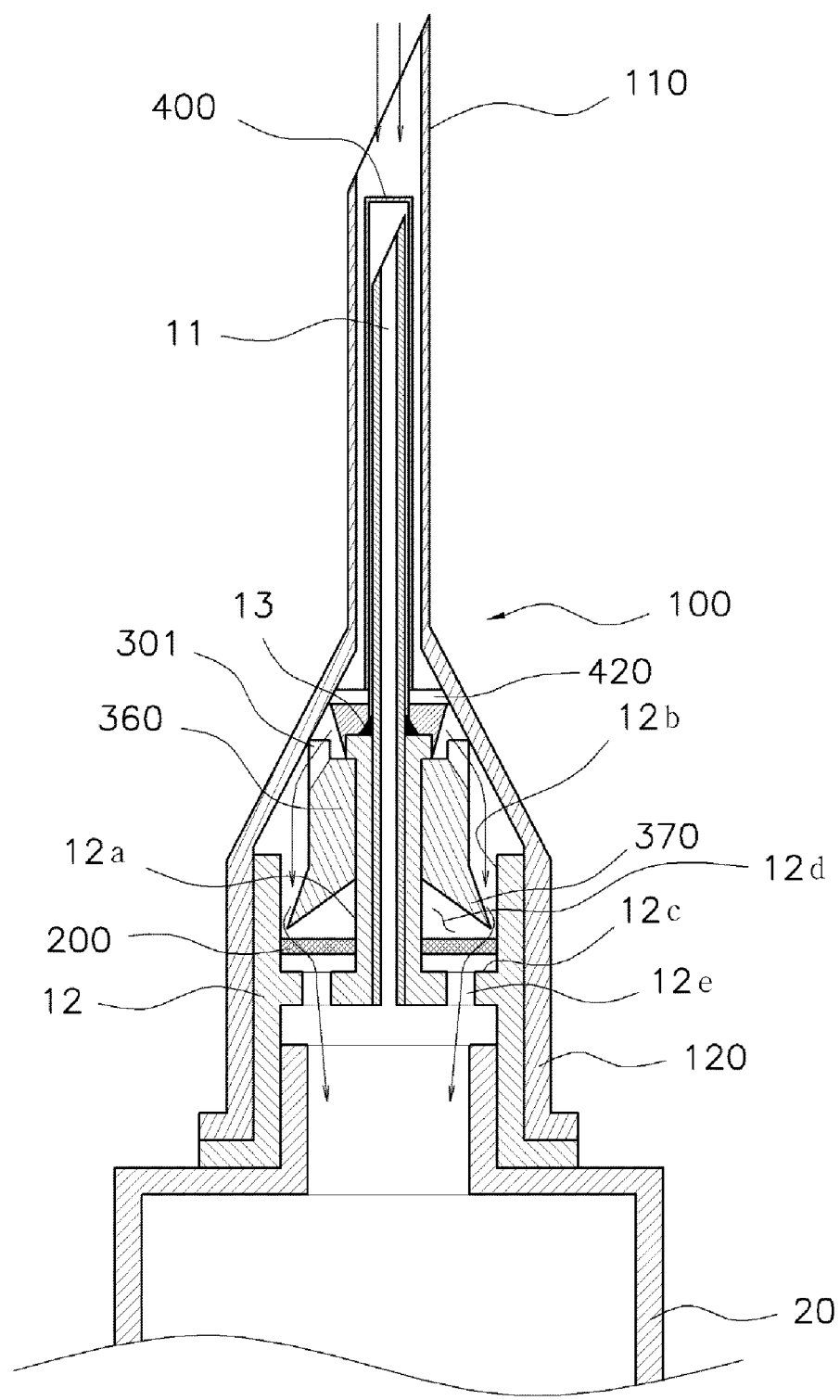
FIG. 24 is a sectional view illustrating a still further example of the one-way valve means in the other example of the first embodiment of the filtering syringe according to the present invention.
Figure 25:
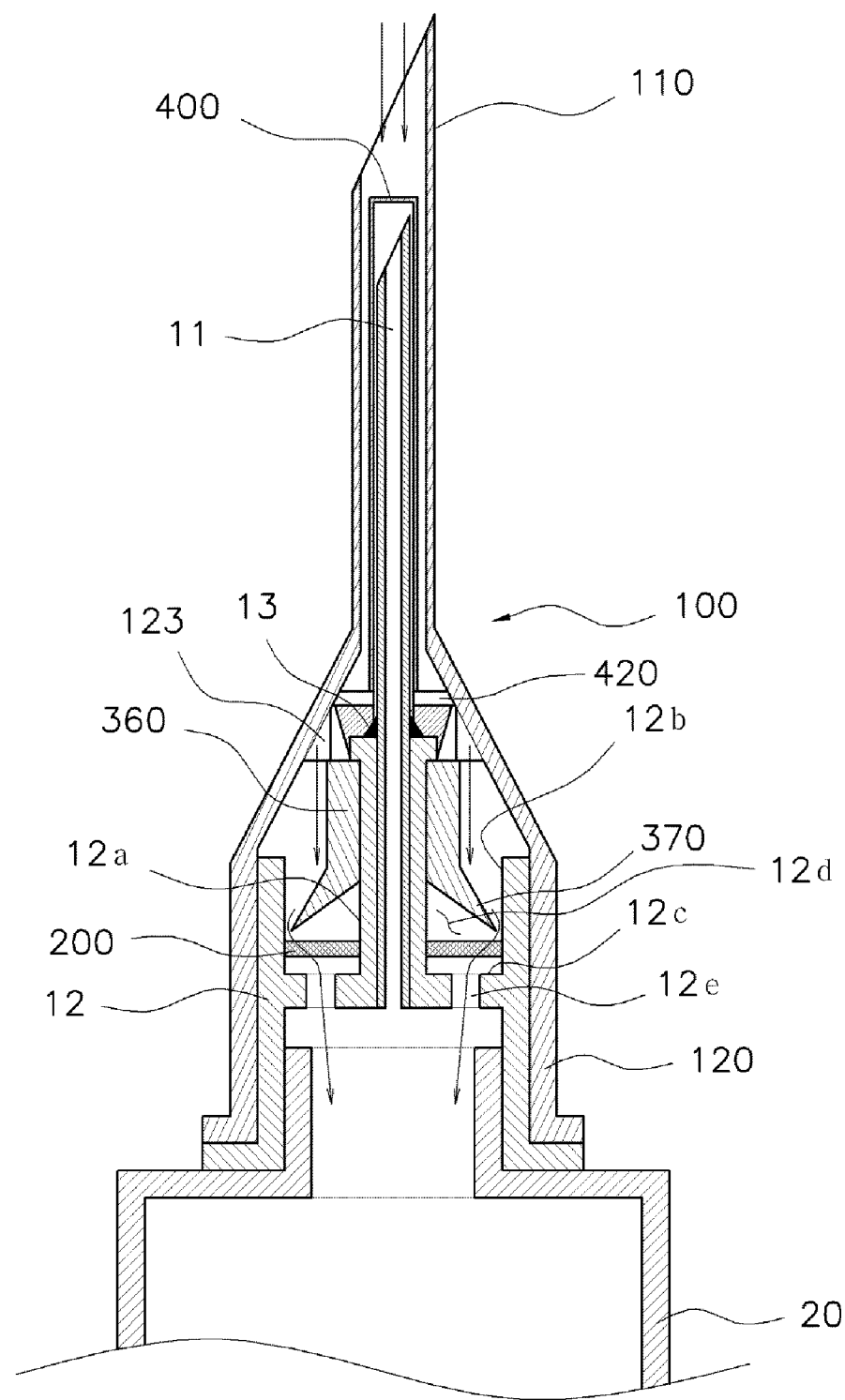
FIG. 25 is a sectional view illustrating another example of a cap in the other example of the first embodiment of the filtering syringe according to the present invention.

Finally, FIG. 24 is a sectional view illustrating a still further example of the one-way valve means in the other example of the first embodiment of the filtering syringe according to the present invention, and FIG. 25 is a sectional view illustrating another example of a cap in the other example of the first embodiment of the filtering syringe according to the present invention.

As shown in FIGS. 4 to 20, the filtering syringe of the present invention is technically characterized in that a suction flow passage for sucking a liquid medicine and an injection flow passage for injecting the liquid medicine are formed inside and outside a well-known syringe such that a flow passage from a liquid medicine-container to a filter means 200 is formed independently of the injection flow passage and an outer peripheral surface of an injection needle 10, thereby basically preventing the liquid medicine containing foreign substances from being injected and enabling the liquid medicine to be easily sucked with a force less than that required for a conventional syringe.

Embodiments of the present invention will be described below in detail with reference to the accompanying drawings.

With improvement of a well-known syringe including the injection needle 10, a cylinder 20 and a plunger, the filtering syringe of the present invention is provided with the suction flow passage from the liquid medicine-container to the cylinder 20, and the injection flow passage from the cylinder 20 to the injection needle 10, wherein the filter means 200 and a one-way valve means 300 are provided in the suction flow passage and a detachable opening/closing means 400 is provided in the injection flow passage. Preferably, a flow passage from the liquid medicine-container to the filter means 200 in the suction flow passage is formed independently of the outer peripheral surface of the injection needle 10 and the injection flow passage.

As such, the flow passage from the liquid medicine-container to the filter means 200 is a section in which a portion of the liquid medicine containing foreign substances such as glass fragments produced upon opening of the liquid medicine-container such as a glass ampoule may remain. By causing this section in which the foreign substances may remain to be formed independently of the outer peripheral surface of the injection needle as well as the injection flow passage as described above, it is possible to fundamentally prevent foreign substances such as glass fragments from being injected into the body.

In other words, an inlet of the suction flow passage and an outlet of the injection flow passage are formed independently of each other in the present invention. Upon suction of the liquid medicine, the one-way valve means 300 in the suction flow passage is opened, so that the liquid medicine from which foreign substances are removed by the filter means 200 is sucked into the cylinder 20 of the syringe and the opening/closing means 400 closes the injection flow passage during the suction.

On the contrary, upon injection of the liquid medicine, the suction flow passage is closed by the one-way valve means 300, while the injection flow passage is opened by removing the opening/closing means 400.

According to the embodiments, opening or closing of the one-way valve means 300 may be automatically adjusted depending on a direction of pressure on the liquid medicine, may be adjusted in response to a user's rotation manipulation, or may be adjusted depending on simply whether a cap 100 is separated.

In implementing the filtering syringe of the present invention as described above, there may be the following four examples depending on combinations of whether the inlet of the suction flow passage and the outlet of the injection flow passage are coaxially arranged with each other and whether an outlet of the suction flow passage and an inlet of the injection flow passage are shared on the cylinder 20 of the syringe. These examples will be described below by classifying them into first to fourth embodiments.

First embodiment: Example in which the inlet of the suction flow passage and the outlet of the injection flow passage are coaxially arranged with each other, and the outlet of the suction flow passage and the inlet of the injection flow passage are shared.

Second embodiment: Example in which the inlet of the suction flow passage and the outlet of the injection flow passage are not coaxially arranged with each other, and the outlet of the suction flow passage and the inlet of the injection flow passage are shared.

Third embodiment: Example in which the inlet of the suction flow passage and the outlet of the injection flow passage are coaxially arranged with each other, and the outlet of the suction flow passage and the inlet of the injection flow passage are not shared.

Fourth embodiment: Example in which the inlet of the suction flow passage and the outlet of the injection flow passage are not coaxially arranged with each other, and the outlet of the suction flow passage and the inlet of the injection flow passage are not shared.

(1) First Embodiment

Example in which the inlet of the suction flow passage and the outlet of the injection flow passage are coaxially arranged with each other, and the outlet of the suction flow passage and the inlet of the injection flow passage are shared.

The first embodiment of the filtering syringe according to the present invention may be classified into an example in which both the filter means 200 and the one-way valve means 300 are embedded in the filtering syringe and an example in which at least one of the filter means 200 and the one-way valve means 300 is externally provided.

First, the example of the first embodiment of the filtering syringe according to the present invention in which both the filter means 200 and the one-way valve means 300 are embedded in the filtering syringe is illustrated in FIGS. 4 to 11.

In particular, FIGS. 4 and 5 show the filtering syringe employing the one-way valve means 300, which is automatically opened and closed depending on a direction of pressure on the liquid medicine, wherein the suction flow passage consists of a suction needle 110 of the cap 100→the filter means 200→a cap hub 120 of the cap 100→the one-way valve means 300→a hub 12 of the injection needle 10→the cylinder 20.

The cap 100 is to suck the liquid medicine from the liquid medicine-container, and includes the suction needle 110 and the cap hub 120. A sharp tip of the suction needle 110 is inclined to penetrate a vial or the like and is made of a metal material or a synthetic resin material so that it has a high strength.

In addition, the cap hub 120 is integrally coupled to and supports the suction needle 110, wherein the filter means 200 may be embedded in the cap hub, and an inner peripheral surface of the cap hub 120 is coupled to an outer peripheral surface of the hub 12 that supports a needle body 11 of the injection needle 10, thereby maintaining airtightness.

Here, the needle body 11 and the hub 12 of the injection needle 10 are fixed to each other by an adhesive material 13 such as epoxy, wherein the hub 12 is hermetically assembled to the cylinder 20 of the syringe.

A sealing means 600 such as a separate elastic seal may be additionally provided between the inner peripheral surface of the cap hub 120 and the outer peripheral surface of the hub 12 to prevent the liquid medicine from leaking through a gap therebetween, and the filter means 200 has a well-known configuration capable of filtering foreign substances such as fine glass fragments.

In addition thereto, the one-way valve means 300 that is automatically opened or closed depending on the direction of pressure on the liquid medicine is embedded in the hub 12 of the injection needle 10.

This one-way valve means 300 may include a circular elastic plate 310, which is made of, for example, a flexible material such as silicone, and a stepped portion 311.

The elastic plate 310 is formed to have a diameter corresponding to an inner diameter of the hub 12 so that a center portion of the elastic plate is assembled and fixed to the hub 12, and the stepped portion 311 is formed above an outer peripheral edge of the elastic plate 310 so as to limit upward deformation of the elastic plate 310.

As a result, upon suction of the liquid medicine, the one-way valve means 300 is opened while the outer peripheral edge of the elastic plate 310 is deformed downward as shown in FIG. 4, so that the cylinder 20 of the syringe is filled with the liquid medicine.

Moreover, as shown in FIG. 5, the injection flow passage consists of the cylinder 20→the hub 12 of the injection needle 10→the needle body 11 of the injection needle 10.

Since the outer peripheral edge of the elastic plate 310 in the one-way valve means 300 is contacted with the stepped portion 311 to limit upward deformation of the elastic plate 310 as shown in FIG. 5, the one-way valve means 300 is closed to prevent the liquid medicine from leaking to the suction flow passage.

In addition thereto, although the needle body 11 of the injection needle 10 is closed by the opening/closing means 400 upon suction of the liquid medicine, the opening/closing means 400 is separated to open the needle body 11 upon injection of the liquid medicine.

In particular, in the present invention, the opening/closing means 400 may be configured to include a hermetic space 410 and a flange 420 as shown in FIG. 6.

In other words, the opening/closing means 400 has functions of closing the needle body 11 of the injection needle 10 upon suction of the liquid medicine and of opening the needle body 11 of the injection needle 10 upon injection of the liquid medicine. In the present invention, it is preferable that the opening/closing means 400 can be coupled to the hub 12 of the injection needle 10.

To this end, the hermetic space 410 is formed at a lower portion of the opening/closing means 400 so that the hermetic space 410 may surround and be coupled to the hub 12 of the injection needle 10.

In particular, in the present invention, it is preferable that an adhesive material 13 for incorporating the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

With this configuration, it is possible to prevent degradation of an adhesive force of the adhesive material 13 due to contact of the adhesive material 13 with the liquid medicine, or alteration of components of the liquid medicine caused by the adhesive material 13.

In addition thereto, the flange 420 provided in the opening/closing means 400 enables the opening/closing means 400 to be assembled to the inner peripheral surface of the cap hub 120, if necessary, and can also be used to cause the filter means 200 to be embedded in the cap hub 120.

FIG. 5 illustrates that the filter means 200 is installed on the flange 420 of the opening/closing means 400 and this the opening/closing means 400 is fixedly installed within the cap 100 so that the opening/closing 400 is separated together with the cap 100 in response to separation of the cap 100, thereby opening the injection needle 10.

Accordingly, upon suction of the liquid medicine, the liquid medicine is sucked from the cap 100 into the cylinder through the filter means 200 and the one-way valve means 300, and upon injection of the liquid medicine, the liquid medicine is injected from the cylinder 20 through the injection needle 10.

As a result, since the suction flow passage upstream of the filter means 200 is completely separated from the outer peripheral surface of the injection needle 10 as well as the injection flow passage, injection of foreign substances such as glass fragments remaining in the injection flow passage or around the injection needle 10 is fundamentally prevented.

Next, an example in which the opening or closing of the one-way valve means 300 in the first embodiment of the filtering syringe according to the present invention is adjusted in response to a user's rotation manipulation will be described with reference to FIGS. 7 to 9.

Even in this case, the suction flow passage consists of the suction needle 110 of the cap 100→the filter means 200→the cap hub 120 of the cap 100→the one-way valve means 300→the hub 12 of the injection needle 10→the cylinder 20.

Although it is shown that the filter means 200 may be provided in the suction needle 110 of the cap 100, this case puts limitation on the size of the filter means 200, thereby requiring a larger force for suction of the liquid medicine. Therefore, it is more preferable to provide the filter means 200 at the flange 420 of the opening/closing means 400 as previously described.

Furthermore, description of a configuration overlapping with that of the embodiment in which the one-way valve means 300, which is automatically opened or closed depending on the direction of pressure on the liquid medicine as described above, is employed will be omitted. An operation of the one-way valve means 300 which is different from that in the previous embodiment will be described below.

In this case, the hub 12 of the injection needle 10 is formed to be bisected in a vertical direction as shown in FIG. 9, and a disk-shaped rotary plate 320 which constitutes a part of the hub 12 is integrally formed at a lower portion of the needle body 11.

A plurality of through-holes 321 through which the liquid medicine may pass are formed circumferentially equidistantly on a certain radius in the rotary plate 320. FIG. 9 shows that four through-holes 321 are formed with a phase angle difference of 90 degrees, and the rotary plate is rotatable about a center of the needle body 11.

Here, if the through-holes 321 are sized to be large, the liquid medicine is more smoothly sucked, but a rotation angle of the rotary plate 320 for adjusting the opening or closing will be increased accordingly. On the contrary, if the through-holes 321 are sized to be small, the number of the through-holes 321 is increased, whereby the rotation angle of the rotary plate 320 for adjusting the opening or closing will be reduced accordingly.

Rotary protrusions 322 radially extend on an upper surface of the rotary plate 320 so that a user may adjust a rotation of the rotary plate 320. Thus, the rotary protrusions 322 are assembled within guide grooves 121 longitudinally formed on the inner peripheral surface of the cap hub 120.

As a result, when the cap hub 120 of the cap 100 is externally rotated, the rotary plate 320 is rotated therein together with the cap hub in response to the rotation of the cap hub.

Also, the rotary plate 320 is assembled to be seated on a lower portion of the bisected hub 12 in a state where a fixing disk 330 formed of a sealable material is placed between the rotary plate and the lower portion of the hub. Through-holes 331 and 340 corresponding to the aforementioned through-holes 321 of the rotary plate 320 are also formed in the fixing disk 330 and the lower portion of the bisected hub 12, respectively.

Accordingly, when the through-holes 321 formed in the rotary plate 320 are aligned in a straight line with the through-holes 331 and 340 formed in the fixing disk 330 and the lower portion of the bisected hub 12 in response to the rotation of the rotary plate 320, the one-way valve means 300 is opened as shown in FIG. 7, and otherwise, the one-way valve means 300 is closed as shown in FIG. 8.

Here, to prevent the fixing disk 330 from being rotated together with the rotary plate 320 in response to the rotation of the rotary plate 320, it is preferable to form a rotation-preventing recess 332 on an edge of the fixing disk 330 and to form a rotation-preventing projection 341 on the lower portion of the bisected hub 12, which corresponds to the rotation-preventing recess.

Moreover, a securing ledge 342 having an annular cross-section is formed on the hub 12 so that that the rotary plate 320 may be rotated in a state where the rotary plate 320 is assembled to the lower portion of the bisected hub 12 with the fixing disk 330 interposed therebetween.

As a result, as shown in FIGS. 7 and 8, the fixing disk 330 and the rotary plate 320 may be stacked inside the securing ledge 342 to maintain an assembled state thereof.

In addition, in order to enable a user to confirm whether the through-holes 321 of the rotary plate 320 and the through-holes 331 and 340 of the fixing disk 330 and the hub 12 are aligned in a straight line, a protrusion 323 having a hemispherical cross-section may be formed to upwardly protrude on an edge of the rotary plate 320 as shown in FIG. 9, and a recess (not shown) corresponding to the protrusion may be formed on an inner bottom surface of the securing ledge 342 of the hub 12.

Accordingly, when the through-holes 321 of the rotary plate 320 and the through-holes 331 and 340 of the fixing disk 330 and the hub 12 are aligned in a straight line, a user can confirm whether the through-holes are aligned, by using a distinction feeling generated when the protrusion 323 resiliently enters the recess.

Similarly, if two types of recesses having different depths are alternately arranged, a user may also recognize that the through-holes are aligned and the one-way valve means 300 is in an open state when the user experiences a greater distinction feeling or that the through-holes are not aligned and the one-way valve means 300 is in a closed state when the user experiences a smaller distinction feeling.

As a result, the user can intermittently control the opening or closing of the one-way valve means 300 by an external manipulation for rotating the cap hub 120 of the cap 100. When the liquid medicine is sucked but not immediately injected into the body, for example, when a saline solution is sucked and then injected into a liquid medicine-container for accommodating a powdered medicament so that the powdered medicament is dissolved and subsequently a resulting liquid medicine is sucked again, there is an advantage in that suction and injection may be smoothly performed with a smaller force by the aforementioned one-way valve means 300 of which the opening or closing is intermittently controlled depending on the rotation of the cap hub.

Thereafter, when the liquid medicine is intended to be injected into the body and thus the one-way valve means 300 in the open state is closed by such rotation, the injection flow passage consists of the cylinder 20→the hub 12 of the injection needle 10→the needle body 11 of the injection needle 10 as shown in FIG. 8.

Even in this case, although not shown in the figure, the opening/closing means 400 is fixedly installed within the cap 100 to allow the opening/closing means 400 to be separated together with the cap 100 in response to separation of the cap 100, thereby enabling the injection needle 10 to be opened.

Accordingly, upon suction of the liquid medicine, the liquid medicine is sucked from the cap 100 into the cylinder 20 through the filter means 200 and the one-way valve means 300, whereas upon injection of the liquid medicine, the liquid medicine is injected from the cylinder 20 through the injection needle 10.

As a result, it is possible to quickly suck and then rapidly discharge the liquid medicine, as required.

Next, an example in which the opening or closing of the one-way valve means 300 in the first embodiment of the filtering syringe according to the present invention is controlled depending on simply whether the cap 100 is separated will be described with reference to FIGS. 10 and 11.

Even in this case, the suction flow passage consists of the suction needle 110 of the cap 100→the filter means 200→the cap hub 120 of the cap 100→the one-way valve means 300→the hub 12 of the injection needle 10→the cylinder 20.

In this case, the hub 12 of the injection needle 10 is provided with flow holes 351 formed to extend from the inner peripheral surface to the outer peripheral surface of the hub as shown in FIGS. 10 and 11, and a groove 352 is formed on the outer peripheral surface of the hub 12 along an entire perimeter of the hub around the flow holes 351.

The diameter and number of the flow holes 351 may be appropriately changed such that the liquid medicine may flow smoothly and airtightness may be achieved, and the groove 352 is formed to have two steps with different depths. An elastic band 350 made of an elastic material such as rubber and having a generally circular cross-section is placed in the groove 352.

This elastic band 350 is elastically disposed in the groove 352 so that the position of the elastic band may be moved depending on whether the elastic band is in contact with the cap hub 120 of the cap 100.

To this end, an engagement ledge 122 for contact with the elastic band 350 is formed on the inner peripheral surface of the cap hub 120.

Accordingly, in a state where the cap 100 is assembled to the injection needle 10, as shown in FIG. 10, the elastic band 350 is brought into contact with the engagement ledge 122 and then moved, so that the flow holes 351 are opened.

On the contrary, in a state where the cap 100 is separated from the injection needle 10, as shown in FIG. 11, the elastic band 350 is contracted to its minimum diameter and then returned to its original position, so that the flow holes 351 are closed.

As a result, the user can intermittently control the opening or closing of the one-way valve means 300 depending on whether the cap 100 is assembled. When it is intended that the saline solution is sucked and then injected into the liquid medicine-container for accommodating the powdered medicament so that the powdered medicament is dissolved and subsequently the resulting liquid medicine is sucked again as described above, there is an advantage in that suction and injection may be smoothly performed with a smaller force by the aforementioned one-way valve means 300.

Subsequently, when the liquid medicine is intended to be injected into the body and thus the cap 100 is simply separated, the injection flow passage consists of the cylinder 20→the hub 12 of the injection needle 10→the needle body 11 of the injection needle 10, as shown in FIG. 11.

Even in this case, the opening/closing means 400 is fixedly installed within the cap 100 to allow the opening/closing means 400 to be separated together with the cap 100 in response to the separation of the cap 100, thereby enabling the injection needle 10 to be opened.

Accordingly, upon suction of the liquid medicine, the liquid medicine is sucked from the cap 100 into the cylinder 20 through the filter means 200 and the one-way valve means 300, whereas upon injection of the liquid medicine, the liquid medicine is injected from the cylinder 20 through the injection needle 10.

As a result, it is possible to quickly suck and then rapidly discharge the liquid medicine, as required.

FIG. 20 shows that two one-way valve means 300 are formed in a dual configuration. In this case, a first one-way valve means 300 formed with modified flow holes 351 and groove 352 may be provided on the hub 12 of the injection needle 100, and opening or closing of the first one-way valve means 300 can be controlled depending on whether the cap 100 is assembled. A second one-way valve means 300 comprised of an elastic plate 310 having a modified shape may be provided within the hub 12.

As for the second one-way valve means 300, the elastic plate 310 does not require the separate stepped portion 311 and is brought into direct contact with an inner wall of the hub 12 depending on the direction of pressure on the liquid medicine, thereby performing the opening or closing of the second one-way valve means 300.

As such, it is also possible to configure the filtering syringe by including two or more one-way valve means 300.

Next, an example in which at least one of the filter means 200 and the one-way valve means 300 in the first embodiment of the filtering syringe according to the present invention is externally provided will be illustrated in FIGS. 12 to 14.

Although the examples in which the filter means 200 and the one-way valve means 300 are embedded in the cap 100 or the injection needle 10 have been described above, most of a force required for sucking the liquid medicine is utilized when the liquid medicine passes through the filter means 200 and the one-way valve means 300.

That is, although the filter means 200 and the one-way valve means 300 are necessarily designed to be large in size so as to perform suction of the liquid medicine with a smaller force, both the filter means 200 and the one-way valve means 300 are embedded in a conventional syringe, whereby there is limitation on enlargement of the filter means 200 and the one-way valve means 300 in size.

Therefore, in the present invention, it is possible to add an external suction flow passage extending from the cap hub 120 of the cap 100 to the cylinder 20 of the syringe as shown in FIGS. 12 to 14.

In this manner, it is possible to eliminate limitation on the sizes of the filter means 200 and the one-way valve means 300.

FIG. 12 illustrates an example in which the filter means 200 is embedded in the hub 12, whereas the one-way valve means 300 is separately provided outside.

In this case, the one-way valve means 300 may be variously modified to, for example, a check valve having a ball embedded therein and no limitation on the size thereof, other than the aforementioned examples.

A separate structure for forming a flow passage between the cap 100 and the cylinder 20 may be added.

For example, a manifold may be formed integrally with each of the cap hub 120 and the cylinder 20 and the manifolds of them may be then connected by a tube made of a flexible material to each other. In addition, the manifolds may be configured to be at certain angles and may also have a well-known configuration enabling selective connection or disconnection of the manifolds from each other.

In the configuration for disconnecting the manifolds from each other, there would no leakage of the liquid medicine only if a state where the one-way valve means 300 is connected to the cylinder 20 should be maintained.

Moreover, although FIG. 12 shows that only the one-way valve means 300 is externally provided, both the filter means 200 and the one-way valve means 300 may also be externally provided, as illustrated in FIG. 13.

Furthermore, FIG. 14 shows an example in which the one-way valve means 300 is externally provided by using a separate connector 500.

In this case, the connector 500 may be formed integrally with the cap hub 120 or the cylinder 20, the filter means 200 or the one-way valve means 300 may be embedded in the connector 500, and there will be no limitation on modification thereof.

(2) Second Embodiment

Example in which the inlet of the suction flow passage and the outlet of the injection flow passage are not coaxially arranged with each other, and the outlet of the suction flow passage and the inlet of the injection flow passage are shared.

Next, the second embodiment of the present invention is a case in which the outlet of the suction flow passage and the inlet of the injection flow passage are shared, whereas the inlet of the suction flow passage and the outlet of the injection flow passage are not coaxially arranged with each other.

To this end, the cap 100 and the injection needle 10 are independently placed, and the opening/closing means 400 is separated from the cap 100 and is provided to close the injection needle 10.

In this case, as shown in FIG. 15, the filter means 200 may be provided in the cap 100 and the one-way valve means 300 may be provided on the suction flow passage. Although not shown, the filter means 200 may be separated from the cap 100 and both the filter means 200 and the one-way valve means 300 may then be provided on the suction flow passage.

The suction flow passage extending from the cap 100 to the cylinder 20 may be flexibly configured, although it will be also possible to configure this suction flow passage to be maintained at a certain angle different from that of the flow passage from the cylinder 20 to the injection needle 10.

Accordingly, the suction flow passage may be formed at one of bodies branched at different angle from the cylinder 20, and the injection flow passage may be formed at the other of the bodies.

With this configuration, the liquid medicine is sucked through the cap 100 in a state where the injection flow passage is closed by the opening/closing means 400, whereby the sucked liquid medicine passes through the filter means 200 and the one-way valve means 300 and fills the cylinder 20 and the liquid medicine to be injected may be discharged to the injection needle 10 from which the opening/closing means 400 has been removed.

FIG. 16 shows a configuration in which the separate connector 500 is added, and FIG. 16 illustrates the connector 500 having a perpendicular branch, but the connector may be configured to have a differently angled branch, or it is also preferable to configure the connector to have an angle-adjustable branch.

(3) Third Embodiment

Example in which the inlet of the suction flow passage and the outlet of the injection flow passage are coaxially arranged with each other, and the outlet of the suction flow passage and the inlet of the injection flow passage are not shared.

FIGS. 17 and 18 illustrate a case in which the inlet of the suction flow passage and the outlet of the injection flow passage are coaxially arranged with each other as described above, whereas the outlet of the suction flow passage and the inlet of the injection flow passage are not shared.

FIG. 17 shows a case in which only the one-way valve means 300 is externally provided, and FIG. 18 shows a case in which both the one-way valve means 300 and the filter means 200 are externally provided.

Even in this case, a manifold may be formed integrally with each of the cap hub 120 and the cylinder 20 and the manifolds of them may be then connected by a tube made of a flexible material to each other. In addition, the manifolds may be configured to be at certain angles and may also have a well-known configuration enabling selective connection or disconnection of the manifolds from each other.

In the configuration for disconnecting the manifolds from each other, there would no leakage of the liquid medicine only if a state where the one-way valve means 300 is connected to the cylinder 20 should be maintained.

(4) Fourth Embodiment

Example in which the inlet of the suction flow passage and the outlet of the injection flow passage are not coaxially arranged with each other, and the outlet of the suction flow passage and the inlet of the injection flow passage are not shared.

Finally, the fourth embodiment is a case in which, as shown in FIG. 19, the inlet of the suction flow passage and the outlet of the injection flow passage are not coaxially arranged with each other, and the outlet of the suction flow passage and the inlet of the injection flow passage are not shared.

Although FIG. 19 shows the example in which the filter means 200 and the one-way valve means 300 are embedded in the cap 100, the one-way valve means 300 or both the filter means 200 and the one-way valve means 300 may be formed in the flow passage extending from the cap 100 to the cylinder 20 or may be provided in the cylinder 20.

As a result, foreign substances contained in the liquid medicine sucked into the cap 100 are removed while the liquid medicine passes through the filter means 200, the liquid medicine is then sucked into the cylinder 20 through the one-way valve means 300, and the liquid medicine in the cylinder 20 can be injected into the body via the injection needle 10 by removing the opening/closing means 400.

In another example of the first embodiment according to the present invention, the hub 12 constituting a part of the injection needle 10 is formed with an annular space 12*d* having an inner wall surface 12*a*, an outer wall surface 12*b* and a bottom surface 12*c* as shown in FIG. 21.

This annular space 12*d* is an empty space defined by rotating a generally U-shaped cross-section through 360 degrees about the needle body 11, wherein an outer peripheral surface surrounding the needle body 11 corresponds to the inner wall surface 12*a*, an inner peripheral surface of the hub 12 constitutes the outer wall surface 12*b*, and a horizontal surface connecting the inner wall surface 12*a* and the outer wall surface 12*b* constitutes the bottom surface 12*c*.

In this case, through-holes 12*e* are formed in the bottom surface 12*c* so that the liquid medicine may pass through the through-holes 12*e* and into the cylinder 20.

In particular, a one-way valve means 300 and the filter means 200 are placed within the annular space 12*d*.

The one-way valve means 300 is a component that is automatically opened or closed depending on a direction of pressure on the cylinder 20, is made of, for example, a flexible elastic material such as silicone and includes a cylindrical portion 360 and a wing portion 370 as shown in FIG. 21.

Here, the cylindrical portion 360 is configured to secure the one-way valve means 300, and surrounds and is coupled to the hub 12 of the injection needle 10. In this case, it is preferable that the hub 120 is formed with a stepped portion for preventing the one-way valve means 300 from being separated.

Moreover, an inclined lower end of the wing portion 370 is elastically contact with the outer wall surface 12*b*.

As a result, upon suction of the liquid medicine, an edge of the wing portion 370 is deformed downward as shown in FIG. 22 so that the one-way valve means 300 is opened, and upon injection of the liquid medicine, the edge of the wing portion 370 is brought into contact with the outer wall surface 12*b* of the annular space 12*d* as shown in FIG. 23 so that the one-way valve means 300 is closed.

Furthermore, the well-known filter means 200 capable of filtering foreign substances such as fine glass fragments is provided within the annular space 12*d* between the one-way valve means 300 and the through-holes 12*e*.

Accordingly, upon suction of the liquid medicine, the liquid medicine that has passed through the one-way valve means 300 is filtered by the filter means 200 to remove foreign substances and then flows into the cylinder 20 through the through-holes 12*e* of the annular space 12*d*.

In this case, the cap 100 is a component for sucking the liquid medicine from the liquid medicine-container, and includes the suction needle 110 and the cap hub 120. The sharp tip of the suction needle 110 is inclined to penetrate a vial or the like and is made of a metal material or a synthetic resin material so that it has a high strength.

Furthermore, the cap hub 120 is a component formed integrally with the suction needle 110 to support the suction needle 110, and the inner peripheral surface of the cap hub 120 is coupled to the outer peripheral surface of the hub 12, which supports the needle body 11 of the injection needle 10, to maintain airtightness.

In this case, the opening/closing means 400 surrounding the needle body 11 is provided within the cap 100 as shown in FIG. 21.

This opening/closing means 400 basically functions to open or close the needle body 11 as well as to prevent an exterior of the needle body 11 from being contaminated by the contaminated liquid medicine.

In other words, although the needle body 11 of the injection needle 10 was closed by the opening/closing means 400 upon suction of the liquid medicine, the opening/closing means 400 is separated to open the needle body 11 upon injection of the liquid medicine.

Particularly, in the present invention, it is possible to configure the opening/closing means 400 to include the hermetic space 410 and the flange 420.

With this configuration, the opening/closing means 400 is fixedly installed the inner peripheral surface of the cap hub 120 of the cap 100 via the flange 420 so that the opening/closing means 400 may be integrally separated together with the cap 100.

In particular, in the present invention, it is preferable that the adhesive material 13 for incorporating the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

Accordingly, it is possible to prevent degradation of an adhesive force of the adhesive material 13 due to contact of the adhesive material 13 with the liquid medicine, or alteration of components of the liquid medicine caused by the adhesive material 13.

With this configuration, the suction flow passage of the liquid medicine consists of the space between the cap 100 and the opening/closing means 400→the one-way valve means 300→the filter means 200→the through-holes 12e→the cylinder 20, and the injection flow passage of the liquid medicine consists of the cylinder 20→the injection needle 10.

As for the filtering syringe of the present invention described above, the opening or closing of the one-way valve means 300 depends on the direction of pressure on the cylinder 20, wherein when a negative pressure acts on the cylinder 20, the wing portion 370 of the one-way valve means 300 is spaced apart from the outer wall surface 12b as shown in FIG. 22, so that the liquid medicine introduced between the cap 100 and the opening/closing means 400 flows into the cylinder 20 through the opened one-way valve means 300, the filter means 200 and the through-holes 12e.

On the contrary, when a positive pressure acts on the cylinder 20 in a state where the cap 100 and the opening/closing means 400 are separated, the wing portion 370 of the one-way valve means 300 comes in contact with the outer wall surface 12b as shown in FIG. 23, so that the liquid medicine in the cylinder 20 does not pass through the closed one-way valve means 300 but is injected through the injection needle 10.

Although the one-way valve means 300 has been described above as being opened or closed depending on only the direction of pressure on the cylinder 20, there may be a structure for assisting in opening the one-way valve means 300 depending on whether the cap 100 is assembled.

To this end, it is preferable that, as shown in FIG. 24, a projection 301 cooperating with an inner peripheral surface of the cap 100 is formed on the one-way valve means 300 to promote deformation of the wing portion 370.

That is, the projection 301 is formed to protrude from an upper portion of the one-way valve means 300, and the projection is designed to have such a height that when the cap 100 is assembled, the projection comes in contact with the inner peripheral surface of the cap 100. As the cap 100 is assembled, the inner peripheral surface of the cap 100 comes in contact with the projection 301, whereby the wing portion 370 of the one-way valve means 300 may be deformed to induce the opening of one-way valve means 300.

In this case, a flow passage is defined with a certain gap at the projection 301 so as not to block a flow of the liquid medicine.

Of course, it is also possible to form the projection 301 to extend directly from the wing portion 370.

On the contrary, as shown in FIG. 25, a protrusion 123 cooperating with the one-way valve means 300 may be formed on the inner peripheral surface of the cap 100 to promote deformation of the wing portion 370.

In this case, the protrusion 123 is formed on the inner peripheral surface of the cap 100, and the protrusion preferably has such a height and location that it comes in contact with the one-way valve means 300 when the cap 100 is assembled.

With this configuration, the cylindrical portion 360 of the one-way valve means 300 is forced downward to induce downward deformation of the wing portion 370, so that the opening of the one-way valve means 300 may be promoted.

Even in this case, a flow passage is defined with a certain gap at the protrusion 123 so as not to block a flow of the liquid medicine.

In addition, it is also possible to form the protrusion 123 such that it extends to come in direct contact with the wing portion 370, whereby the wing portion 370 is forcibly spaced apart from the outer wall surface 12b by the protrusion 123.

Therefore, the filtering syringe of the present invention has great advantages in that the inlet of the suction flow passage and the outlet of the injection flow passage are completely separated from each other so that foreign substances such as glass fragments may be fundamentally prevented from being sucked together with the liquid medicine, and in that since the filter means 200 and the one-way valve means 300 may be externally provided, as required, there is no limitation on the sizes of the filter means 200 and the one-way valve means 300, whereby the suction of the liquid medicine can be smoothly performed with a smaller force.

The aforementioned embodiments are merely examples for specifically explaining the spirit of the present invention, and the scope of the present invention is not limited to the figures and embodiments.

| [Explanation of Reference Numerals] | |
|---|---|
| 10: Injection needle | 11: Needle body |
| 12: Hub | 12a: Inner wall surface |
| 12b: Outer wall surface | 12c: Bottom surface |
| 12d: Annular space | 12e: Through-hole |
| 13: Adhesive material | 20: Cylinder |
| 30: Plunger | 100: Cap |
| 110: Suction needle | 120: Cap hub |
| 121: Guide groove | 122: Engagement ledge |
| 123: Protrusion | 200: Filter means |
| 300: One-way valve means | 301: Projection |
| 310: Elastic plate | 311: Stepped portion |
| 320: Rotary plate | 321: Through-hole |
| 322: Rotary protrusion | 323: Protrusion |
| 330: Fixing disk | 331: Through-hole |
| 332: Rotation-preventing recess | 340: Through-hole |
| 341: Rotation-preventing projection | 342: Securing ledge |
| 350: Elastic band | 351: Flow hole |
| 352: Groove | 360: Cylindrical portion |
| 370: Wing portion | 400: Opening/closing means |
| 410: Hermetic space | 420: Flange |
| 500: Connector | 600: Sealing means |

The invention claimed is:

1. A filtering syringe comprising an injection needle, a cylinder and a plunger, the filtering syringe further comprising:
a suction flow passage formed from a liquid medicine-container to the cylinder, the liquid medicine-container being used to contain liquid medicine;
an injection flow passage formed from the cylinder to the injection needle;
a filter means and a one-way valve means provided within the suction flow passage; and
a detachable opening/closing means provided on the injection flow passage such that the detachable opening/closing means is coupled to close the injection needle during suction of the liquid medicine and removed to open the injection needle upon injection of the liquid medicine,
wherein a flow passage portion of the suction flow passage extending from the liquid medicine-container to the filter means is formed in the detachable opening/closing means to be isolated from an outer peripheral surface of the injection needle and the injection flow passage,
wherein an inlet of the suction flow passage and an outlet of the injection flow passage are coaxially arranged with each other, and an outlet of the suction flow passage and an inlet of the injection flow passage are shared, wherein:

a hub of the injection needle is formed with an annular space having an inner wall surface, an outer wall surface and a bottom surface, the bottom surface being formed with through-holes to communicate with the cylinder;

the one-way valve means made of an elastic material and having a cylindrical portion and a wing portion is provided on the inner wall surface, an end of the wing portion being in elastic contact with the outer wall surface;

the filter means is provided within the annular space between the one-way valve means and the though-holes; and the filtering syringe further comprises a cap comprised of a hollow body with a sharp tip and air-tightly coupled to an outer peripheral surface of the hub, the detachable opening/closing means surrounding a needle body of the injection needle being provided within the cap.

2. The filtering syringe of claim 1, wherein an adhesive material for incorporating the needle body of the injection needle and the hub of the injection needle to each other is accommodated in the detachable opening/closing means so that the adhesive material is isolated from the liquid medicine, the detachable opening/closing means surrounding the injection needle to maintain airtightness.

* * * * *